US012805707B2

(12) United States Patent
Zhang

(10) Patent No.: US 12,805,707 B2
(45) Date of Patent: Nov. 24, 2026

(54) METHODS AND SYSTEMS FOR DISPOSABLE ENDOSCOPE

(71) Applicant: Noah Medical Corporation, San Carlos, CA (US)

(72) Inventor: Jian Zhang, Redwood City, CA (US)

(73) Assignee: Noah Medical Corporation, San Carlos, CA (US)

( * ) Notice: Subject to any disclaimer, the term of this patent is extended or adjusted under 35 U.S.C. 154(b) by 464 days.

(21) Appl. No.: 18/054,784

(22) Filed: Nov. 11, 2022

(65) Prior Publication Data

US 2023/0076439 A1 Mar. 9, 2023

Related U.S. Application Data

(63) Continuation of application No. PCT/US2021/034022, filed on May 25, 2021.
(Continued)

(51) Int. Cl.
*A61B 1/005* (2006.01)
*A61B 1/00* (2006.01)
*A61B 1/008* (2006.01)

(52) U.S. Cl.
CPC ............ *A61B 1/0052* (2013.01); *A61B 1/008* (2013.01); *A61B 1/00064* (2013.01)

(58) Field of Classification Search
CPC ... A61B 1/0052; A61B 1/008; A61B 1/00064; A61B 1/00087; A61B 1/00124; A61B 1/00128; A61B 1/00142; A61B 1/00154; A61B 1/0055; A61B 1/0057; A61B 1/00105; A61B 1/00103; A61B 1/00108
See application file for complete search history.

(56) References Cited

U.S. PATENT DOCUMENTS 4,669,172 A * 6/1987 Petruzzi .................. B23P 13/00 138/131
5,235,964 A * 8/1993 Abenaim ........... A61B 1/00135 600/462

(Continued)

FOREIGN PATENT DOCUMENTS

CN 1794944 A 6/2006
EP 2721992 A1 4/2014

(Continued)

OTHER PUBLICATIONS

PCT/US21/34022 International Search Report & Written Opinion dated Oct. 18, 2021.

(Continued)

*Primary Examiner* — Anhtuan T Nguyen
*Assistant Examiner* — Shankar Raj Ghimire
(74) *Attorney, Agent, or Firm* — Wilson Sonsini Goodrich & Rosati

(57) ABSTRACT

An endoscope device is provided. The device comprises: an elongate member comprising a proximal end and a distal end, and a camera is located at the distal end of the disposable elongate member; one or more external guiding elements configured to guide an articulation movement of the distal end of the elongate member, and each of the one or more external guiding elements is individually controlled; and a handle component removably attached to the proximal end of the elongate member.

19 Claims, 24 Drawing Sheets

Related U.S. Application Data

(60) Provisional application No. 63/033,404, filed on Jun. 2, 2020, provisional application No. 63/032,140, filed on May 29, 2020.

(56) References Cited

U.S. PATENT DOCUMENTS

| | | | | |
|---|---|---|---|---|
| 5,447,148 | A | 9/1995 | Oneda et al. | |
| 5,733,242 | A * | 3/1998 | Rayburn | A61B 1/0052 600/143 |
| 6,432,042 | B1 * | 8/2002 | Bashour | A61B 1/00154 600/146 |
| 7,811,228 | B2 * | 10/2010 | Adams | A61B 1/126 600/125 |
| 8,052,597 | B2 | 11/2011 | Boulais | |
| 8,702,594 | B2 * | 4/2014 | Edidin | A61B 1/00128 439/38 |
| 10,278,563 | B2 * | 5/2019 | Ouyang | A61B 1/00052 |
| 10,292,571 | B2 * | 5/2019 | Ouyang | A61B 1/00105 |
| 10,433,717 | B1 * | 10/2019 | Truckai | A61B 1/00094 |
| 10,524,636 | B2 * | 1/2020 | Ouyang | A61B 1/00066 |
| 10,616,491 | B2 * | 4/2020 | Haggerty | H04N 23/69 |
| 11,445,890 | B2 * | 9/2022 | Levinson | A61B 1/00131 |
| 11,478,130 | B2 * | 10/2022 | Noyes | A61B 1/00073 |
| 11,503,988 | B2 * | 11/2022 | Wessels | A61B 1/00006 |
| 11,547,280 | B2 * | 1/2023 | Ulmschneider | A61B 1/00128 |
| 11,596,297 | B2 * | 3/2023 | Yoshinaga | A61B 1/01 |
| 11,607,112 | B2 * | 3/2023 | Toth | A61B 1/000095 |
| 11,771,312 | B2 * | 10/2023 | Noyes | A61B 1/00117 600/160 |
| 11,889,992 | B2 * | 2/2024 | Taylor | A61B 1/018 |
| 11,937,871 | B2 * | 3/2024 | Crawford | A61B 18/14 |
| 11,986,162 | B2 * | 5/2024 | Moreau | A61B 1/015 |
| 2002/0043266 | A1 * | 4/2002 | Toti | A61M 16/0418 128/207.14 |
| 2005/0075538 | A1 * | 4/2005 | Banik | A61B 1/0052 600/152 |
| 2010/0004633 | A1 | 1/2010 | Rothe et al. | |
| 2010/0280449 | A1 * | 11/2010 | Alvarez | A61B 34/71 606/1 |
| 2011/0021871 | A1 * | 1/2011 | Berkelaar | A61B 1/00105 600/104 |
| 2011/0178367 | A1 * | 7/2011 | Anvari | A61B 1/313 600/106 |
| 2011/0196199 | A1 * | 8/2011 | Donhowe | A61B 5/065 600/102 |
| 2014/0107416 | A1 * | 4/2014 | Birnkrant | A61B 1/00124 600/110 |
| 2014/0180007 | A1 * | 6/2014 | Edidin | A61B 1/05 600/122 |
| 2015/0164595 | A1 * | 6/2015 | Bogusky | A61B 1/018 29/426.1 |
| 2015/0230697 | A1 * | 8/2015 | Phee | A61B 1/0057 901/41 |
| 2018/0008126 | A1 * | 1/2018 | Arai | A61B 1/00133 |
| 2018/0206707 | A9 | 7/2018 | Ouyang et al. | |
| 2018/0256009 | A1 * | 9/2018 | Ouyang | A61B 1/00048 |
| 2019/0246873 | A1 * | 8/2019 | Lu | A61B 1/0623 |
| 2019/0246884 | A1 * | 8/2019 | Lu | A61B 1/00179 |
| 2019/0298460 | A1 * | 10/2019 | Al-Jadda | A61B 1/0057 |
| 2020/0000326 | A1 * | 1/2020 | Truckai | A61B 1/00094 |
| 2020/0077880 | A1 * | 3/2020 | Ouyang | A61B 1/0057 |
| 2020/0110956 | A1 | 4/2020 | Fan et al. | |
| 2021/0068647 | A1 * | 3/2021 | Walen | A61B 1/00066 |
| 2022/0152356 | A1 * | 5/2022 | Kowshik | A61B 34/76 |
| 2022/0296079 | A1 * | 9/2022 | Takahashi | A61B 1/00071 |

FOREIGN PATENT DOCUMENTS

| | | | |
|---|---|---|---|
| WO | WO-2017139604 | A1 | 8/2017 |
| WO | WO-2018125917 | A1 | 7/2018 |
| WO | WO-2021242736 | A1 | 12/2021 |

OTHER PUBLICATIONS

European Patent Application No. 21814485.5 Partial Supplementary European Search Report dated May 15, 2024.

* cited by examiner 901
906
907
908
909

902
910
911

903
912
913

904
914
915

905
916
917
918
919

1807
1808

2006
Thick wall
Thin wall

2007
Thick wall
Thin wall
2008
2001
1807

2002

2003

2004

2005

METHODS AND SYSTEMS FOR DISPOSABLE ENDOSCOPE

REFERENCE

This application is a Continuation Application of International Application No. PCT/US2021/034022, filed May 25, 2021, which claims priority to U.S. Provisional Patent Application No. 63/032,140, filed May 29, 2020, and U.S. Provisional Patent Application No. 63/033,404, filed on Jun. 2, 2020, each of which are entirely incorporated herein by reference.

BACKGROUND OF THE INVENTION

Endoscopes comprise vast applications in diagnosis and treatment of various conditions, such as medical conditions. In common endoscopy diagnosis, an instrument or several separate instruments can be used in combination with the endoscope for biopsies or other treatments. Instruments are usually provided as separate devices from the endoscopes. These instruments may include, for example, mechanical tools such as graspers, scissors, baskets, snares, curette, or advanced instruments such as laser fibers, stitching tools, balloons, morcellators, various implant or stent delivery devices, and the like. Endoscopes and the instruments are often made by different device manufacturers. Even when they are manufactured by the same entity, the endoscope and instrument are manufactured as separate devices due to the cost of the endoscopes and expensive capital equipment.

Endoscopes are traditionally made to be re-usable, which may require thorough cleaning, dis-infection, and/or sterilization after each procedure. In most cases, cleaning, dis-infection, and sterilization may be aggressive processes to kill germs and/or bacteria. Such procedures may also be harsh on the endoscopes themselves. Therefore, the designs of such re-usable endoscopes can often be complicated, especially to ensure that the endoscopes can survive such harsh cleaning, dis-infection, and sterilization protocols. Periodical maintenance and repairs for such re-usable endoscopes may often be needed.

Low cost, disposable medical devices designated for a single use have become popular for instruments that are difficult to clean properly. Single-use, disposable devices are packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction, and sterilization. Traditional endoscopes often include a handle that operators use to maneuver the endoscope. For single-use endoscopes, the handle usually encloses the camera, expensive electronics, and mechanical structures at proximal end in order to transmit the video and allow the users to maneuver the endoscope via a user interface. This may lead to high cost of the handle for a single-use endoscope.

SUMMARY OF THE INVENTION

Recognized herein is a need for an endoscope that allows for performing surgical procedures or diagnostic operations with improved performance and cost-efficiency. Recognized also herein are devices and systems comprising endoscopes which may be disposable and may not require extensive cleaning procedures. The present disclosure provides low-cost single-use articulatable endoscope for diagnosis and treatment in various applications such as bronchoscopy, urology, gynecology, arthroscopy, orthopedics, ENT, gastro-intestine endoscopy, neurosurgery, hysteroscope, cystoscope, resectoscope, and various others. It should be noted that the provided endoscope systems can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

In an aspect, the disclosure provides a device comprising: an elongate member comprising a proximal end and a distal end, where a camera is located at the distal end of the elongate member, and the elongate member comprises at least a portion of a control unit for controlling an articulation of a distal portion of the elongate member; and a handle component removably attached to the proximal end of the elongate member via an interface, where the handle component comprises electronics for processing data transmitted from the camera.

In some embodiments, the handle component is re-usable and the interface between the handle component and the proximal end of the elongate member provides an electric connection. In some embodiments, the interface comprises a locking mechanism to secure a mechanical connection between the handle component and the proximal end of the elongate member. In some embodiments, the elongate member is single-use and the user interface of the control unit is located at the proximal end of the elongate member. In some cases, the user interface comprises a knob, lever or button. In some cases, a mechanical structure for flow management is located at the proximal end of the elongate member.

In some embodiments, the elongate member has adjustable stiffness or to affect the articulation of the distal portion. In some cases, the elongate member comprises a stiffening element and wherein the stiffness of the elongate member is adjusted by adjusting a length of the stiffening element inserted into the elongate member.

In another aspect, the disclosure provides a device comprising: an elongate member comprising a proximal end and a distal end, where a camera is located at the distal end of the elongate member; one or more external guiding elements configured to guide an articulation movement of the distal end of the elongate member, the one or more external guiding elements is individually controlled; and a handle component removably attached to the proximal end of the elongate member. In some embodiments, the elongate member is placed inside the one or more external guiding elements and is movable relative to the one or more external guiding elements.

In some embodiments, each of the one or more external guiding elements comprises an articulation control mechanism for controlling an articulation of the corresponding external guiding element. In some embodiments, a bending direction of the distal end of the elongate member is adjusted by adding or moving the one or more external guiding elements or by configuring a bending direction of the one or more external guiding elements relative to one another. In some embodiments, at least one of the one or more external guiding element is pre-bent.

In another aspect, the disclosure provides a device comprising: an instrument for performing a determined surgical procedure, the instrument comprises a lumen to accept an endoscope; and the endoscope comprising a camera located at a distal tip of the endoscope, the endoscope comprises an articulation control mechanism for controlling the articulation of the device. In some embodiments, the instrument is an endotracheal tube or a Foley catheter. In some embodiments, the instrument and the endoscope are disposable.

In another aspect, the disclosure provides a device comprising: an elongate member comprising a proximal end and a distal end, wherein a camera is located at the distal end of the elongate member, and wherein the elongate member comprises an articulation section formed at least by one or more fluid access holes; and a handle component removably attached to the proximal end of the elongate member, wherein the handle component comprises electronics for processing an image data transmitted from the camera.

In some embodiments, the handle component comprises an electromagnetic (EM) sensor to detect a gravity direction. In some cases, the gravity direction is determined based on sensor data collected from the EM sensor located at the handle component and an EM sensor located at the distal end of the elongate member. In some cases, the gravity direction is used to correct a view of the image data. In some embodiments, the device further comprises a fluid shield connected to the proximal end of the elongate member.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION OF THE INVENTION

Figure 1:
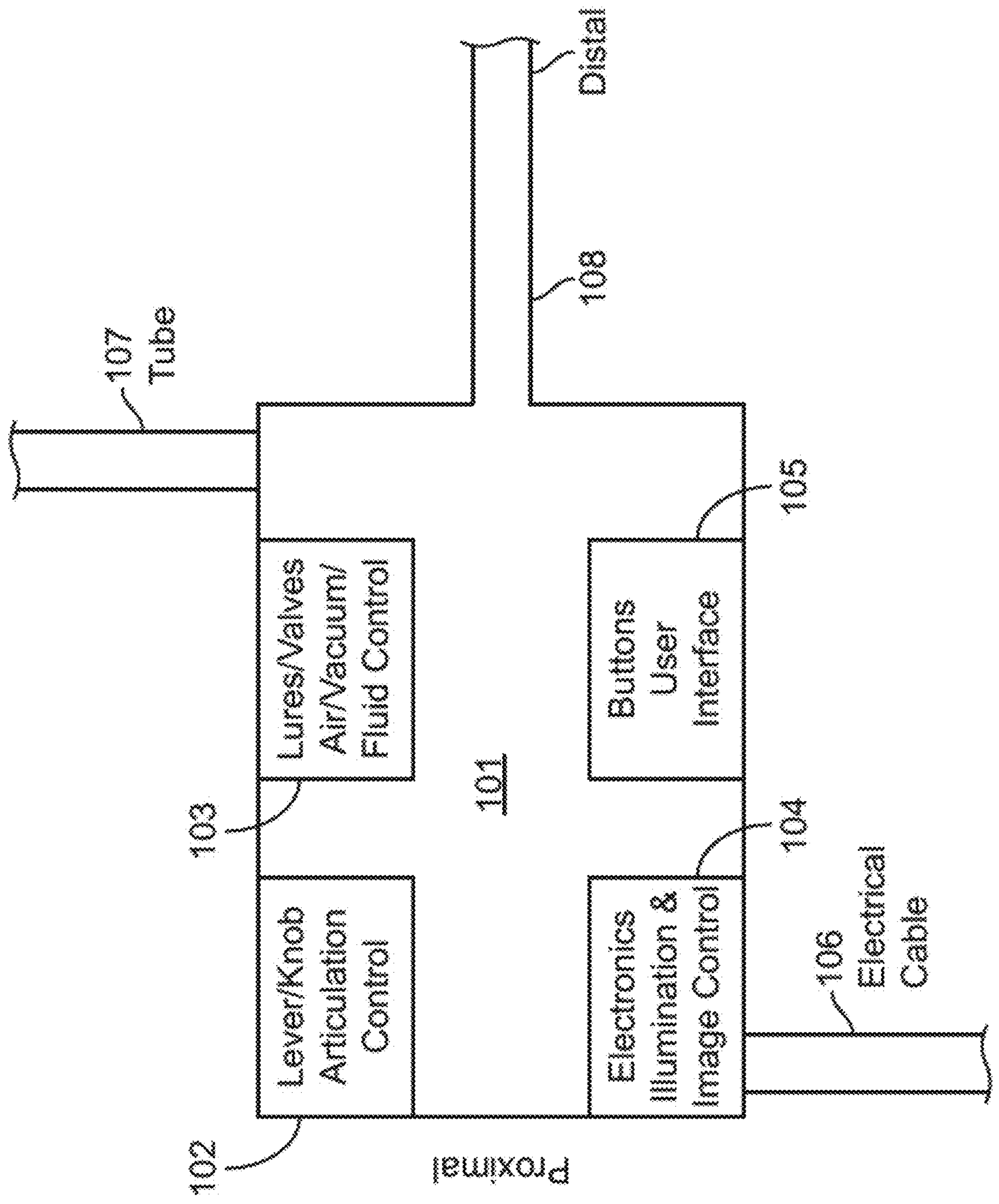
FIG. 1 schematically illustrates a diagram of an exemplary proximal end of an endoscope device.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein a processor encompasses one or more processors, for example a single processor, or a plurality of processors of a distributed processing system for example. A controller or processor as described herein generally comprises a tangible medium to store instructions to implement steps of a process, and the processor may comprise one or more of a central processing unit, programmable array logic, gate array logic, or a field programmable gate array, for example. In some cases, the one or more processors may be a programmable processor (e.g., a central processing unit (CPU) or a microcontroller), digital signal processors (DSPs), a field programmable gate array (FPGA) and/or one or more Advanced RISC Machine (ARM) processors. In some cases, the one or more processors may be operatively coupled to a non-transitory computer readable medium. The non-transitory computer readable medium can store logic, code, and/or program instructions executable by the one or more processors unit for performing one or more steps. The non-transitory computer readable medium can include one or more memory units (e.g., removable media or external storage such as an SD card or random access memory (RAM)). One or more methods or operations disclosed herein can be implemented in hardware components or combinations of hardware and software such as, for example, ASICs, special purpose computers, or general purpose computers.

While exemplary embodiments may be directed to urology, gynecology, rhinology, otology, laryngoscopy, gastroenterology with the endoscopes, combined devices including endoscope and instruments, endoscopes with localization functions, one of skill in the art will appreciate that this is not intended to be limiting, and the devices described herein may be used for other therapeutic or diagnostic procedures and in other anatomical regions of a patient's body, such as eye, stomach, intestine, ovary, and the like, in the forms of: NeuroendoScope, EncephaloScope, OphthalmoScope, OtoScope, RhinoScope, LaryngoScope, GastroScope, EsophagoScope, BronchoScope, ThoracoScope, PleuroScope, AngioScope, MediastinoScope, NephroScope, GastroScope, DuodenoScope, CholeodoScope, CholangioScope, LaparoScope, AmioScope, UreteroScope, HysteroScope, CystoScope, ProctoScope, ColonoScope, ArthroScope, SialendoScope, Orthopedic Endoscopes, and others, in combination with various tools or instruments.

As used herein, the terms distal and proximal may generally refer to locations referenced from the apparatus, and can be opposite of anatomical references. For example, a distal location of an endoscope or catheter may correspond to a proximal location of an elongate member of the patient, and a proximal location of the bronchoscope or catheter may correspond to a distal location of the elongate member of the patient.

A device or endoscope apparatus as described herein, includes an elongate portion or elongate member such as a catheter. The terms "elongate member", "catheter", "endoscope shaft" are used interchangeably throughout the specification unless contexts suggest otherwise. The elongate member can be placed directly into the body lumen or a body cavity.

Endoscopes of the present disclosure can be used to examine the inside of anatomies of subjects, such as animal and human subjects. Subjects may comprise animals such as pig, mouse, dogs, mammals, rodents, monkey, and other animals. Subjects may comprise human subjects, such as patients. The methods and systems provided herein may be used for diagnosing and or treating subjects and/or parts of subjects.

In some embodiments of the present disclosure, a low-cost, single-use, articulating device for diagnosis and treatment is provided. Disposable devices, such as disposable endoscopes may not require post-procedure cleaning, disinfection, and sterilization. Disposable or single-use devices may be disposed after the procedure and save the user valuable time and effort. For example, single-use endoscopes are used only once for each procedure thereby avoiding re-processing after procedure, or risk of causing cross-contamination between patients and reduce infections. In some cases, a single-use endoscope may comprise a disposable catheter removably attached to a re-usable handle component.

In some embodiments of the disclosure, the endoscope may include an optimal design for the proximal end or handle component at reduced cost. The handle component may be re-usable and provided at reduced cost. The proximal end or handle component may have a unique design such that expensive modules are positioned at the re-usable portion. Additionally, the proximal end may include an improved interface mechanism between the single-use catheter and the handle component thereby providing improved modularity and/or convenient assembly. In some embodiments, the endoscope and the handle component are connected via an interface. For example, the interface may provide electrical connection, mechanical connection and/or illumination alignment.

FIG. 1 schematically illustrates a diagram of an exemplary proximal end 101. The proximal end may refer to the proximal end of the endoscope device. For instance, the proximal end may include a handle component or hand piece. The terms "handle component" and "hand piece" can be used interchangeably throughout the specification. The proximal end may be connected to a flexible, articulable shaft or catheter 108.

Navigation of the endoscope through complex and tortuous paths is critical to the success of the examination with minimum pain, side effects, risk or sedation to the patient. Modem endoscopes include means for deflecting the distal tip of the scope to follow the pathway of the structure under examination, with minimum deflection or friction force upon the surrounding tissue. Control cables or pulling cables are carried within the endoscope body in order to connect an articulation section adjacent to the distal end to a set of control knobs at the proximal endoscope handle. By manipulating the control knobs, the operator is usually able to steer the endoscope during insertion and direct it to a region of interest.

In some cases, the proximal end may comprise an articulation control user interface 102 such as lever or knob for controlling the distal articulation of the endoscope. The articulation control user interface may be used to control the bending movement of the distal portion of the catheter in one or more degrees of freedom (e.g., articulation). For example, the turning knob may be connected to the one or more pull wires or control cables to control the direction of the distal articulation structure, and the lever may pull or release the one or more pull wires to control the direction of the articulation structure.

In some cases, the proximal end may comprise a connector such as lures or valves 103 for air, vacuum, or fluid control and/or flow management. For example, a tubular component 107 may be connected to the proximal end via the lures or valves. Any suitable irrigation and aspiration system may connect to the endoscope through the connector 103 (e.g., lures or valves). For example, the irrigation system can inject fluids such as saline and the aspiration system may aspire mucus, saline or other material out of the airways.

The proximal end 101 may comprise electronics for illumination source and imaging control 104. Images/video captured by a camera located at the distal end may be transmitted via the electrical cable 106 connected to the imaging control module 104 located at the proximal end. The imaging control module may comprise one or more processors and electronics for processing the image signal or performing other operations related to image acquisition. For instance, the distal tip may comprise an imaging device such as a camera, and illumination element such as light transmission fibers. The camera may have any display resolution such as full HD, HD, video graphics array (VGA), or less than VGA. The camera may reside at the distal end, and the electrical cable 106 may be connected to the camera to provide power and for data transmission. Light may be transmitted through the light transmitting material or light transmission fibers. In some cases, the proximal end may include one or more user control elements (e.g., Buttons) or other user interfaces 105 for controlling one or more functions of the endoscope.

Any description about the camera, articulation control mechanism, control cables, flow systems, and the like can be applied to other endoscopes, systems, hand piece as described later herein.

Figure 2B:
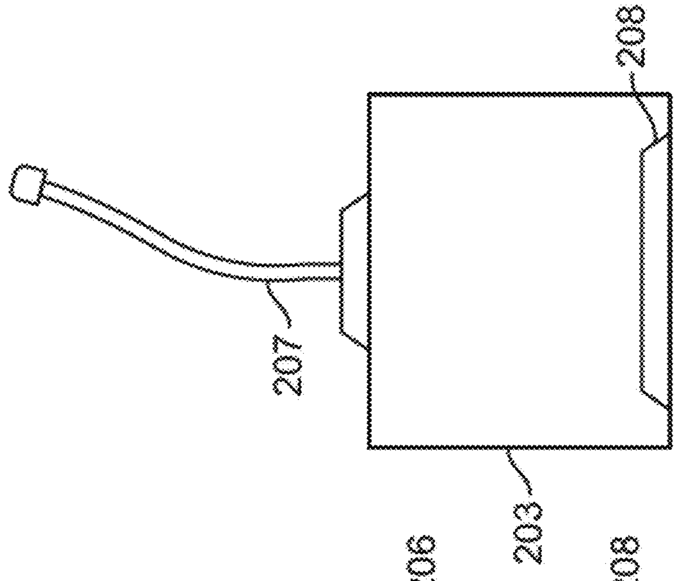
FIGS. 2A-B show an exemplary single-use endoscope with a built-in interface, in accordance with some embodiments of the present disclosure.
Figure 2A:
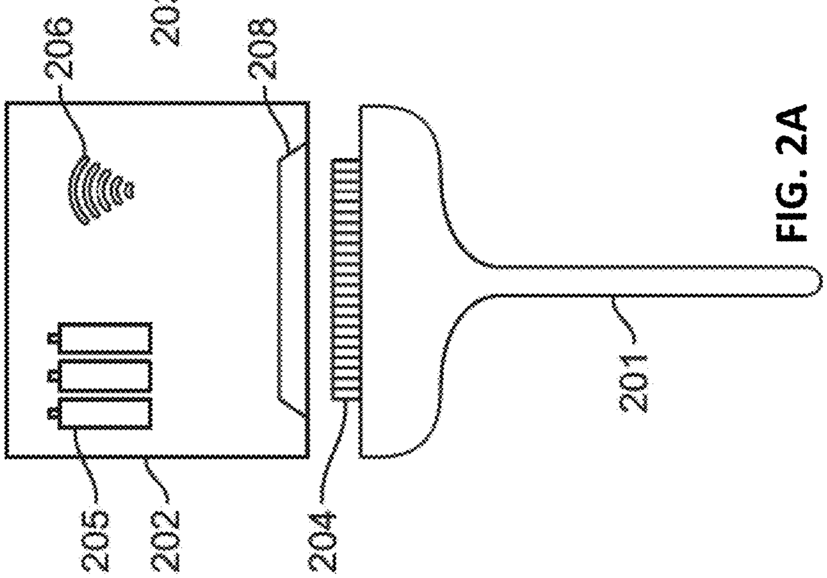

FIGS. 2A-8B show various examples of proximal end for a single-use endoscope, in accordance with some embodiments of the present disclosure. FIG. 2A shows an exemplary single-use endoscope 201 including an interface 204. The disposable endoscope 201 may be removably connected to the hand piece 202, 203 via the interface 204. In some cases, the hand piece 202, 203 may be re-usable and the endoscope 201 may be disposable. In some cases, the endoscope 201 and hand piece 202, 203 may be removably attached such that the endoscope may be released from the hand piece and disposed after single-use while the hand piece can be reused.

The interface 204 may provide mechanical and electrical connection. The interface 204 may include a mechanical interface and an electrical interface. The mechanical interface 204 may allow the endoscope to be releasably coupled to the hand piece. For instance, the handle piece can be attached to the endoscope via quick install/release mechanism, such as magnets and spring-loaded levels. In some cases, the endoscope may be coupled to or released from the hand piece manually without using a tool.

In some cases, the interface 204 may provide electrical connection allowing for electric power and data transmission between the electronics located at the hand piece and the endoscope. The interface 204 may have a uniform design such that it may permit a disposable endoscope to be connected to a wireless handle 202 or a wired handle 203. For example, an endoscope can be connected to both a wireless handle or a wired handle via the same interface.

As mentioned above, the handle component may be a wireless handle 202 or a wired handle 203. The handle component may comprise mating interface 208 to be connected to the interface 204. The example, the interface 204 may comprise pins soldered onto an electronics board such as a printed circuit board (PCB). For instance, receptacle connector (e.g., the female connector) is provided on the hand piece as the mating interface 208. In this case, when the endoscope is plugged into the hand piece, the connection between pins and connectors may provide sufficient mechanical connection force between the endoscope and hand piece, as well as electricity supplied to the endoscope. In another example, the electrical board at the proximal end can be inserted into the receptacle matching connector inside the hand piece. When this connection pair is connected, the light transmission fibers at the proximal end of the endoscope can be aligned with the light source in the hand piece. This interface 204 can provide electrical connection, mechanical connection, as well as alignment of illumination. For instance, power to the camera may be provided by a wired cable terminated at the interface 204. In some cases, the cable wire may be in wire bundle providing power to the camera as well as illumination elements or other circuitry at the distal tip of the endoscope. The camera and/or light source may be supplied with power from a power source 205 disposed in the handle portion via wires, copper wires, or via any other suitable means running through the length of the endoscope. Alternatively, videos and images captured by the camera may be transmitted via wireless communication. It should be noted that any description about the interface can be applied to the devices, endoscopes, systems as described later herein.

The wireless handle component 202 may comprise, for example, a power source (e.g., battery pack) 205 and a wireless communication module 206. The battery pack 205 may be rechargeable or disposable. The power source may provide power to the endoscope and/or electronic components of the endoscope (e.g., camera). The wireless communication module 206 may transmit video signals through secured wireless mechanisms such as WiFi, Bluetooth, RF communication or other forms of communication. The wireless signal may be received by a computer and display the live video from the endoscope. For example, images or videos captured by the camera may be broadcasted to a plurality of devices or systems. In some cases, the hand piece may be designed such that no wires are visible or exposed to operators. FIG. 2B shows the wired handle component 203 may provide wired communication, e.g., cable 207, to the external devices/systems (e.g., computer, display). In some cases, the wired cable 207 may provide power to the endoscope device as well as transmitting the video. Any description about the wired/wireless handle and the components (e.g., power source, communication module) thereof can be applied to other embodiments of hand piece as described elsewhere herein.

Figure 3B:
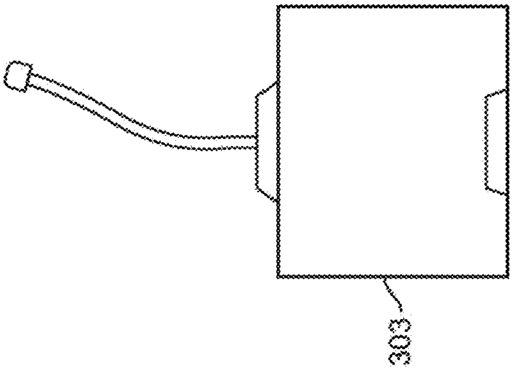
FIGS. 3A-B show an example of a catheter or endoscope shaft with a working channel or fluid channel.
Figure 3A:
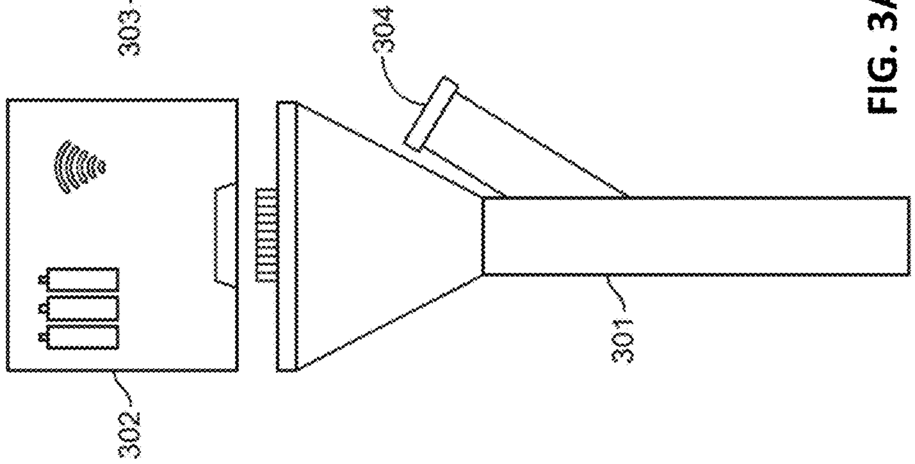

FIGS. 3A-B shows an example of a catheter or endoscope shaft 301 with a working channel or fluid channel 304. The catheter or endoscope shaft 301 may comprise an interface which can be the same as the interface as described in FIGS. 2A-B allowing the endoscope to be removably connected to the re-usable wireless handle 302 or wired handle 303. This may provide an interface with improved flexibility and compatibility across different types of endoscopes and different handle designs.

In some embodiments, the proximal end may have an improved design for the articulation control module at reduced cost. For a flexible endoscope, the distal portion and/or articulation section of the endoscope are typically controlled through pull wires/driving cables, which run from the distal end of the endoscope all the way to the proximal end. The re-usable handle component of the present disclosure may preserve the performance of controlling the articulation of the endoscope while reducing the cost. For example, components such as complex mechanical parts or expensive electronics (e.g., image processing units, electrical boards) may be separated from the low-cost components (e.g., mechanical control user interface, connector or flow management features) and located at the disposable endoscope or the re-usable handle separately to achieve an overall cost reduction.

Figure 4B:
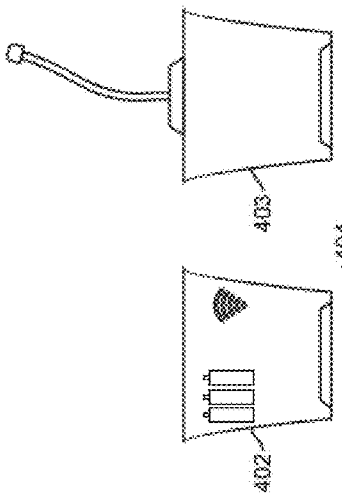
FIGS. 4A-B show an example of a re-usable hand piece connected to a disposable catheter or endoscope shaft.
Figure 4A:
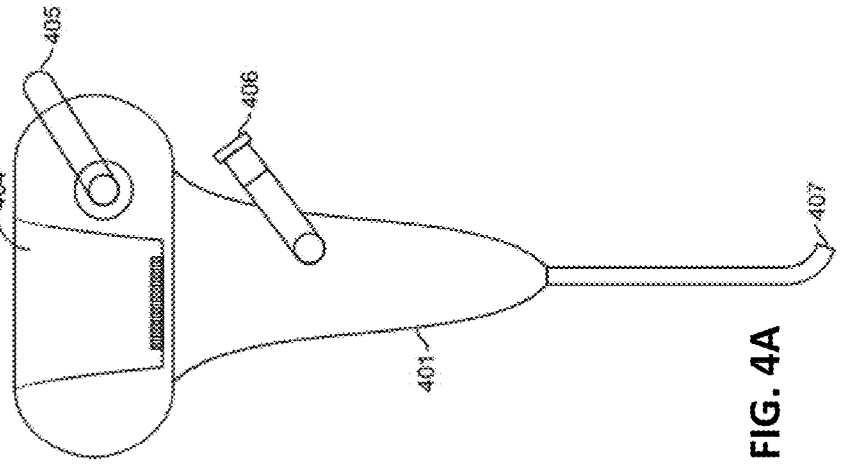
Figure 5:
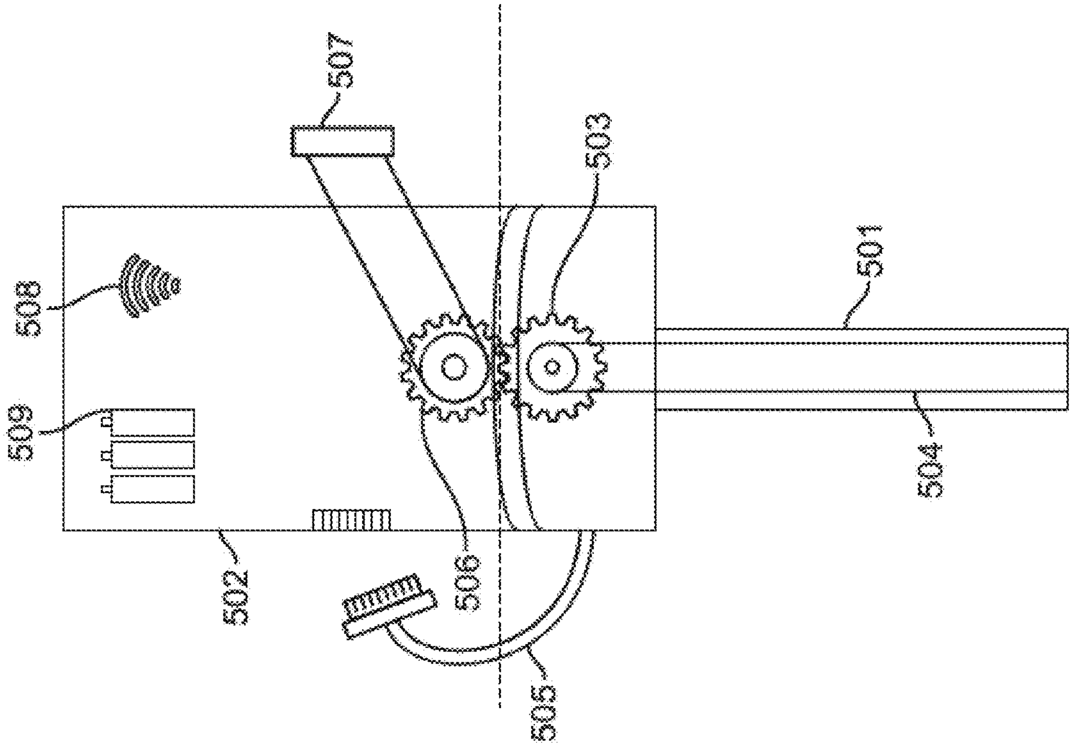
FIG. 5 shows an example of a disposable catheter or endoscope shaft removably coupled to a hand piece.

FIGS. 4A-B and FIG. 5 show exemplary hand pieces with different articulation control modules. The hand piece may be designed such that one or more mechanical control modules such as lure for interfacing the irrigation system/aspiration system and lever/knob for articulation control may be located at the endoscope whereas the electronics for imaging control may be preserved at the hand piece.

FIGS. 4A-B shows an example of a re-usable hand piece 402, 403 connected to a disposable catheter or endoscope shaft 401. The re-usable hand piece such as the wireless hand piece 402 and the wired hand piece 403 can be the same as the handle components as described in FIGS. 2A-B and FIGS. 3A-B. In the illustrated example, the user interface of the articulation control module 405 may be located at the proximal portion of the endoscope. One or more mechanical elements such as a lever may be located at the proximal portion of the endoscope allowing users to pull on the driving cables thereby articulating/bending the tip of the flexible catheter or endoscope shaft 407. In some cases, the connector e.g., lure 406, for interfacing the irrigation/aspiration system may also be located at the proximal portion of the endoscope. This beneficially moves the low-cost machinal components such as connector 406, articulation control user interface 405 to the disposable endoscope while keeping expensive electronics to the re-usable handle piece 402 thereby reducing the cost of the handle. The flexible catheter or endoscope shaft may comprise mating feature 404 at the proximal portion to connect to the hand piece. In this case, the major function of the hand piece may include providing power, illumination and imaging control to the endoscope.

In some cases, a portion of the mechanical elements may be moved to the catheter or endoscope shaft. FIG. 5 shows an example of disposable catheter or endoscope shaft 501 removably coupled to a hand piece 502. In the illustrated example, the disposable catheter or endoscope shaft 501 may not include any mechanical user interfaces (e.g., lever or knob for articulation control). The flexible catheter or endoscope shaft 501 may have a simple mechanical mechanism as part of the articulation driving module at the proximal end of the endoscope. The mechanical mechanism may be a gear 503 that is connected to the driving cables directly and is further connected to a matching mechanical mechanism (e.g., gear 506) located at the hand piece. At the re-usable hand piece 502, the matching mechanical mechanism such as gear 506, may be connected to the mechanical user interface (e.g., lever 507) located at the hand piece 502. In this case, at least part of the articulation control mechanism (e.g., gear 506), the mechanical control user interface (e.g., lever 507), a wireless communication module 508, a battery pack 509 may be located at the re-usable handle, whereas a part of the articulation control mechanism (e.g., gear 503) is located at the catheter or endoscope shaft.

The disposable flexible catheter or endoscope shaft 501 may have the same electric interfaces as described in FIGS. 2A-B or FIGS. 3A-B. Alternatively, the disposable flexible catheter or endoscope shaft 501 may have a separate electric interface such as cable 505 that connects to the re-usable hand piece to supply power and transmit images/videos.

The electrical and mechanical interface between the catheter or endoscope shaft and the handle is a critical interface for signal integrity. The present disclosure provides a proximal end design including an interface with secured connection.

Figure 6A:
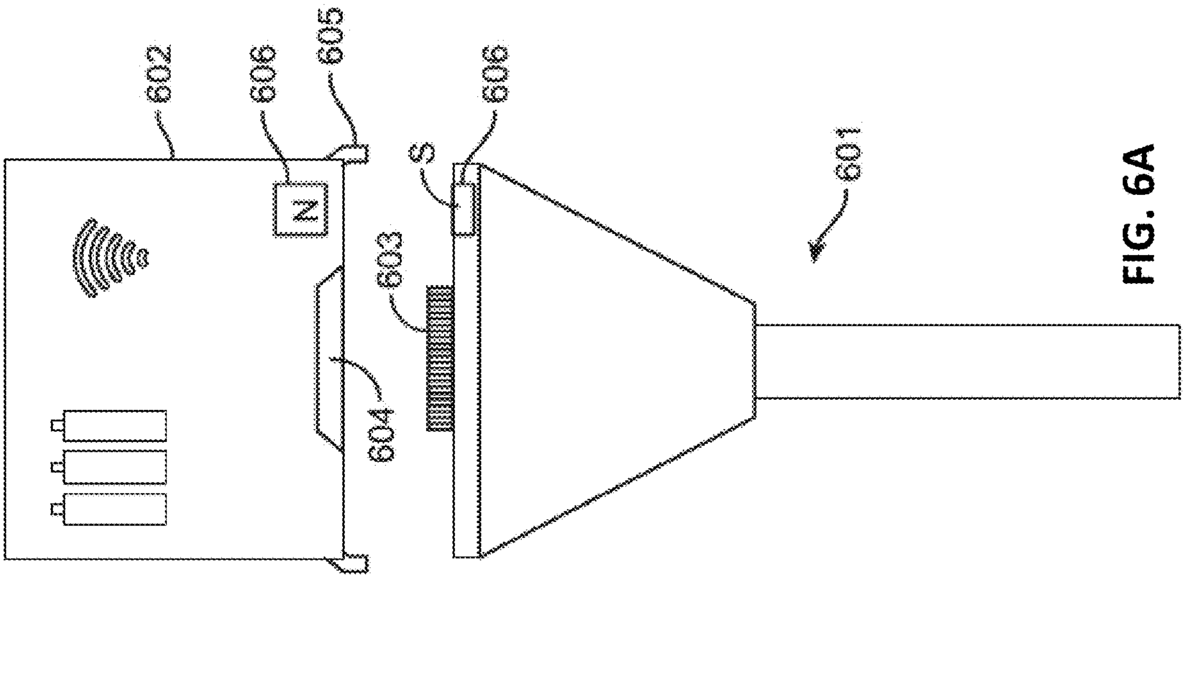
FIGS. 6A-C show examples of an interface with secured connection.
Figure 6B:
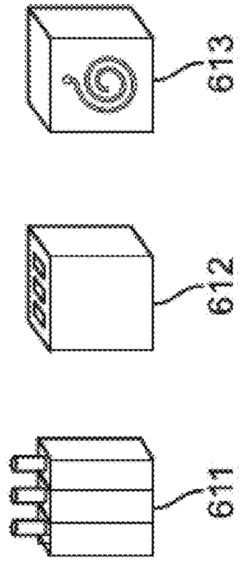
Figure 6C:
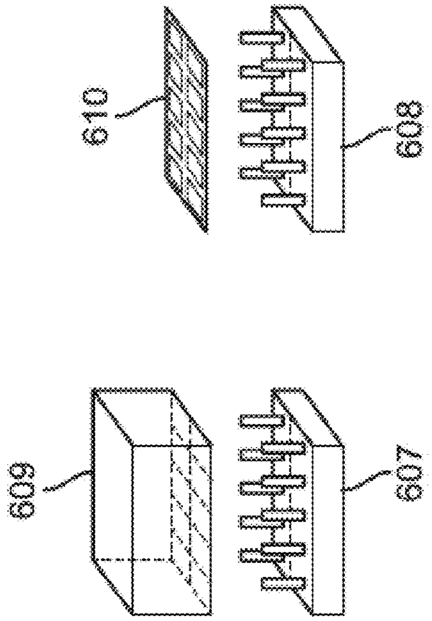

FIGS. 6A-C show examples of the interface between the endoscope shaft and the handle with secured connection. As illustrated in the example in FIG. 6A, the disposable catheter or endoscope shaft 601 may be connected to the re-usable handle 602 through a card edge connector where a PCB board 603 and a mating connector 604 residing on both sides of the catheter and the handle. In some cases, the interface may include a pair of magnets 606 to facilitate the connection between the catheter and the re-usable handle. In some cases, the electrical interface may include a pair of pin connectors 607 and 609. For example, the electrical interface may include a pogo pin connector 608 and a board with surface contacting pads 610.

The mechanical interface may comprise a locking mechanism to secure a mechanical connection between the handle component and the proximal end of the elongate member. For example, the mechanical interface may be secured by a locking mechanism 605. In some examples, the locking mechanism may comprise a quick-release mechanism. In some examples, the one or more mechanical connection features may comprise a snap-on mechanism. Any suitable locking mechanism such as snap, lock, clip, rail, mechanical deformation, mechanical fastening, interlocking connections, flanges, and/or other instruments, tools, and/or mechanisms or any combination thereof can be utilized. This may beneficially assure the reliability of the electric and mechanical connection.

As illustrated in the FIG. 6B, the battery pack may be disposable 611 or chargeable battery 612. In some cases, the battery can be charged through wireless coils 613. For example, a charging station may be configured to transmit charging power to the endoscope shaft or hand piece using inductive transmission. The primary coil 613 can be integrated into the charging station to transmit inductive energy to a secondary coil which is integrated into the hand piece. The secondary coil can be used to charge the one or more batteries of the hand piece.

The management of sterility of these re-usable handles becomes critical in a sterile clinical procedure. In some embodiments, the provided device may further comprise a sterile drape to keep the hand piece sterile during operation. In some cases, the sterile drape is a drape bag. In some cases, the sterile drape further covers the cable of the hand piece.

Figure 7B:
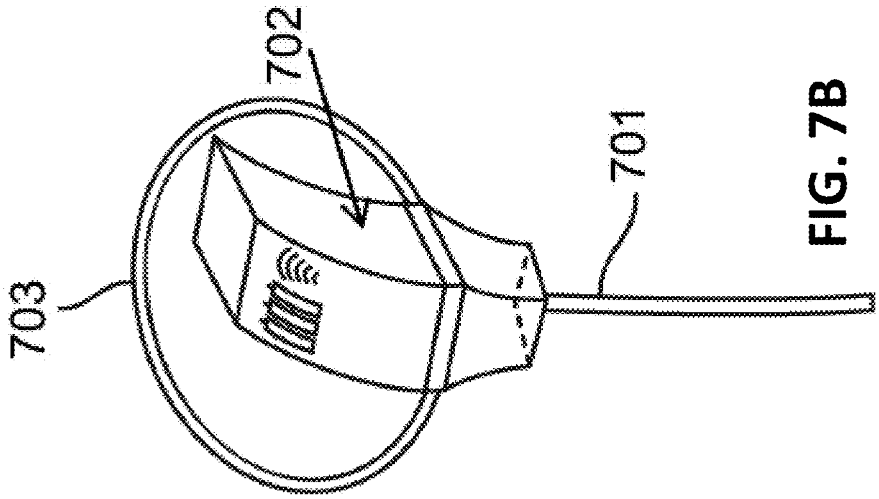
FIGS. 7A-B show examples re-usable handle components protected by a drape.
Figure 7A:
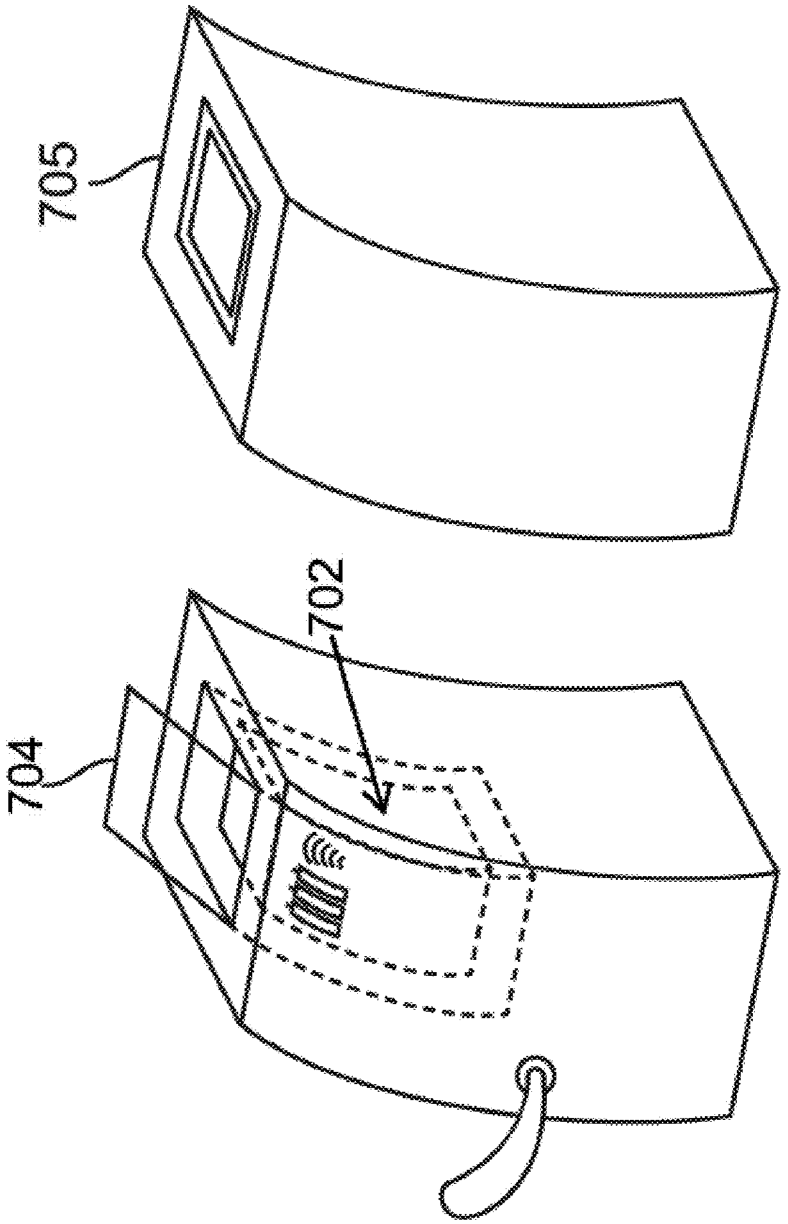

FIGS. 7A-B shows examples of re-usable handle components protected by a drape. As illustrated in the example of FIG. 7B, the disposable catheter or endoscope shaft 701 is connected to the wireless re-usable handle component 702 covered by a sterile drape 703. The sterile drape 703 may be a sterile bag that wraps around the handle component 702 providing a full sterile device to physicians.

In some cases as shown in FIG. 7A, when the handle component comprises the user interface for articulation control (e.g., lever, knob), the sterile drape 705 may have an opening 704 to receive the handle component 702 and is re-sealable during operation. For example, the sterile drape 705 may comprise an exit port with a sealing flange such a user can access the articulation control means. Any suitable means may be used to seal the opening. For example, tapes, zipper, buttons, or sliders may be used to provide a sealed barrier.

Figure 8B:
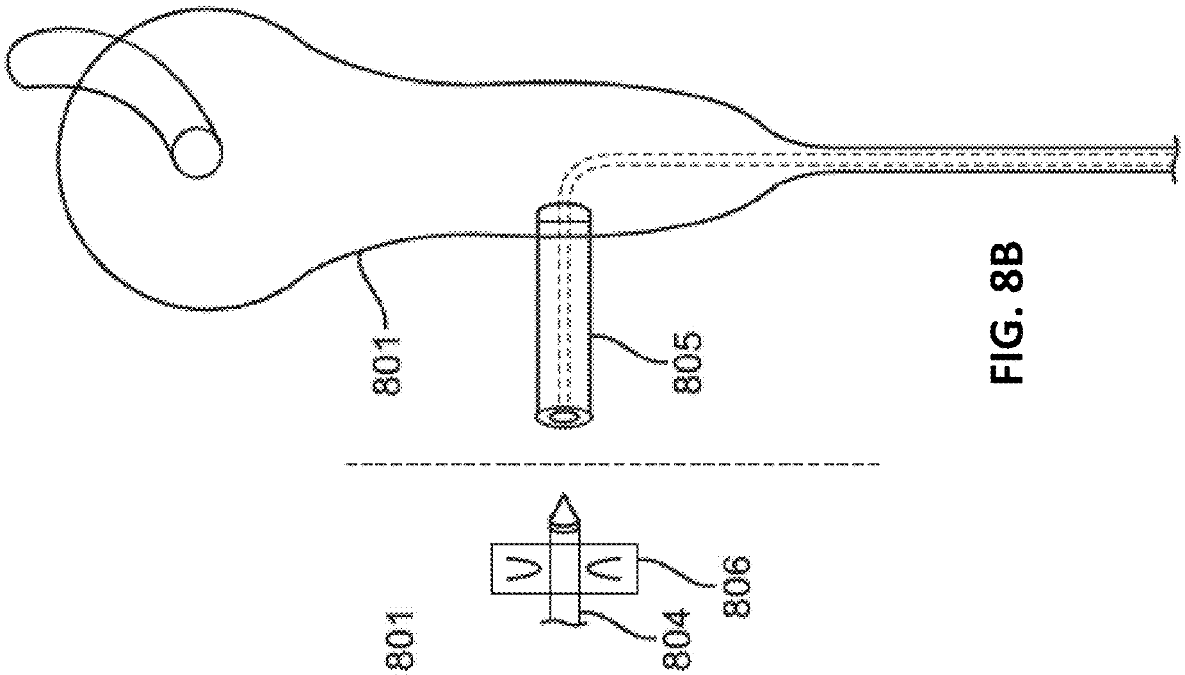
FIGS. 8A-B show various examples of endoscope devices comprising flow management features.
Figure 8A:
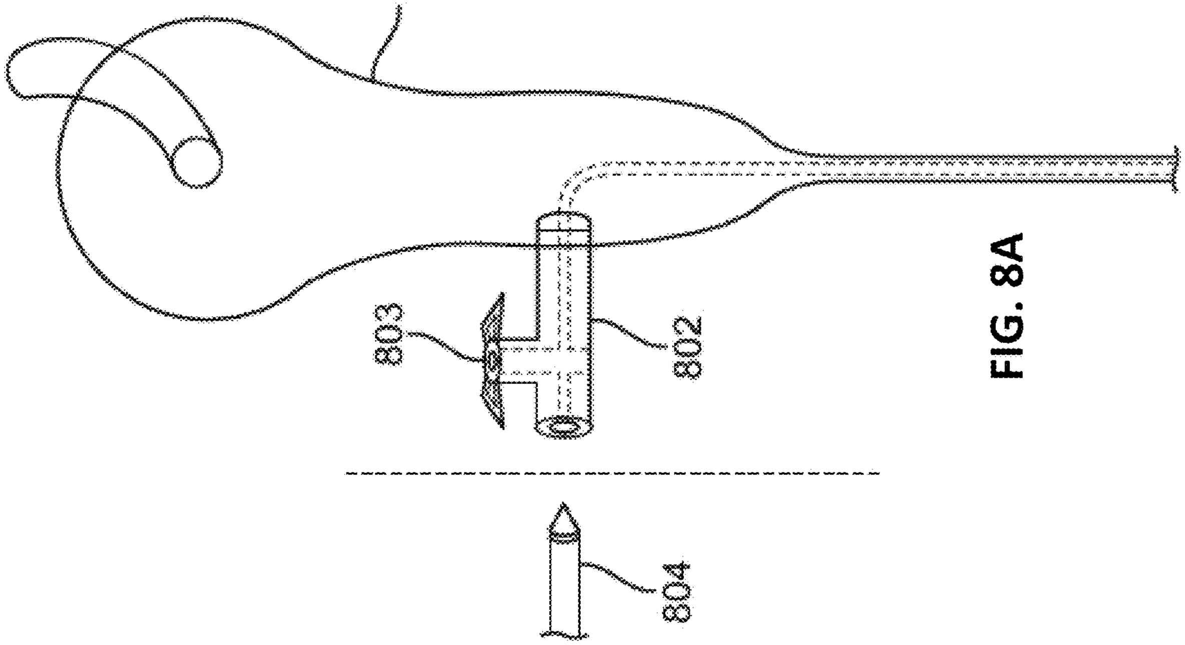

Conventional endoscope devices may be provided with flow control features such as lure or valve to connect to an irrigation and/or aspiration system. The irrigation system can inject fluids such as saline and the aspiration system may aspire mucus or saline or other material out of the airways. FIGS. 8A-B show an example of a conventional endoscope device 801 including a valve 803 for managing flow. An inlet 804 may be connected to the working channel of the endoscope via the connector 802. The flow management features (e.g., valve 803) may be integrated to the connector and is usually disposed along with the single-use endoscope 801.

In some embodiments, the present single-use endoscope may be provided with an alternative flow management feature that is located at the re-usable inlet. As shown in FIG. 8B, flow management features such as pneumatics 806 may be provided to the inlet for air, vacuum or fluid control. Moving the flow management feature 806 from the single-use connector 805 to the re-usable inlet may beneficially lower the cost of the disposable endoscope.

Conventional endoscopes may have a flexible shaft that can be articulated by control cables or pull wires. For instance, the distal end of one or more pull wires may be anchored or attached to the distal portion of the flexible shaft, such that operation of the pull wires by a control unit may apply force or tension to the distal portion which may steer or articulate (e.g., up, down, pitch, yaw, or any direction in-between) at least the distal portion (e.g., flexible section) of the flexible shaft. Traditional articulating structures often require use of additional elements such as a plurality of interconnected segments, pivots, hinges, and the like to achieve articulation. However, such articulating structures can be difficult to clean and/or sterilize because of the complex geometric structures.

In an aspect of the present disclosure, an improved articulation section design for endoscopes are provided. The articulation section may be comprised of low cost, easily mass produced articulation features that allow the distal end of the endoscope to be bent in a desired direction by one or more control cables. Such articulation section may avoid use of articulation joints with complex geometric structures thereby allowing for easy dis-infection and clean.

Figures 9A, 9B, 9C, 9D, 9E:
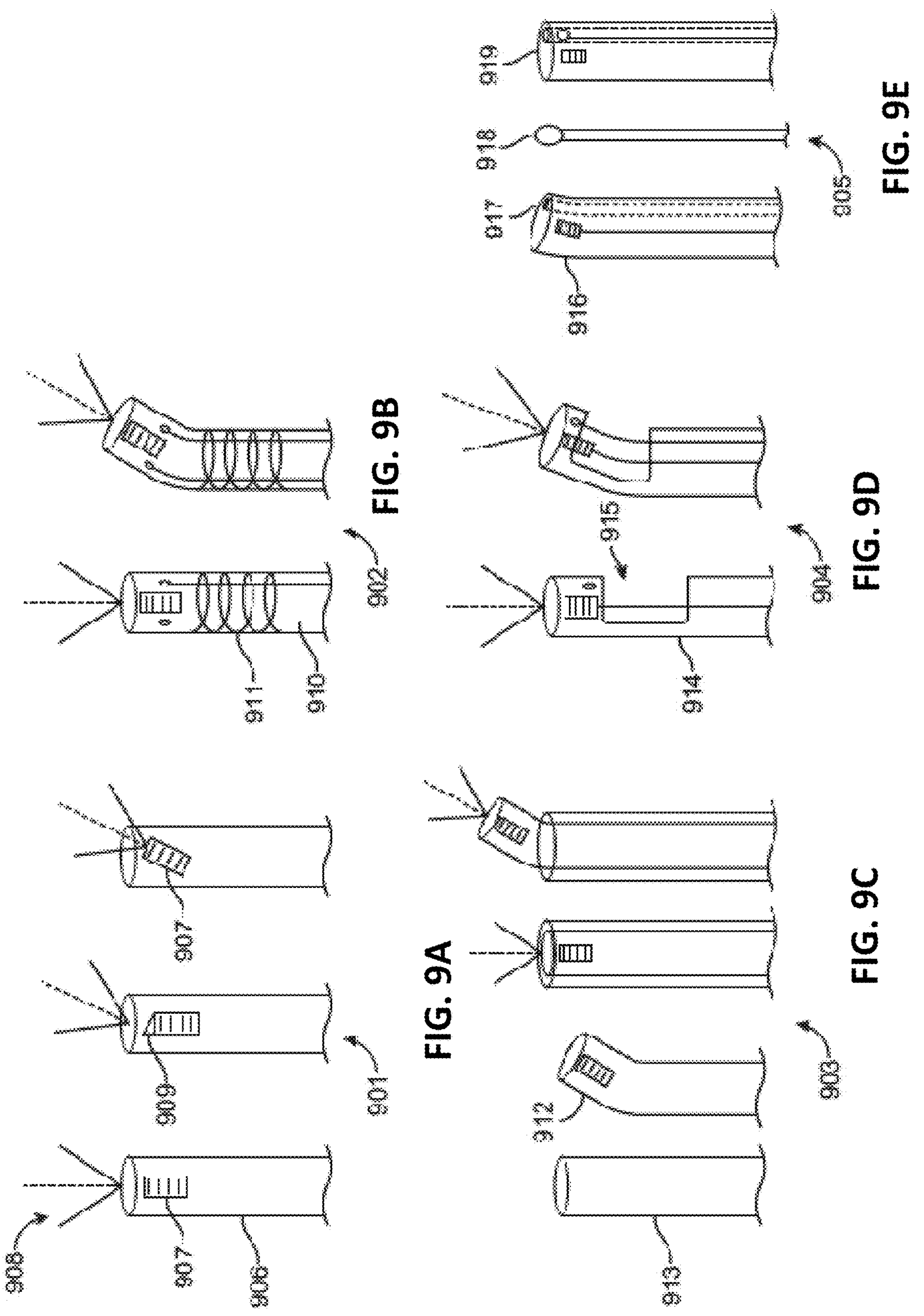
FIGS. 9A-E show various exemplary embodiments of endoscopes with an articulation section.
Figure 10A:
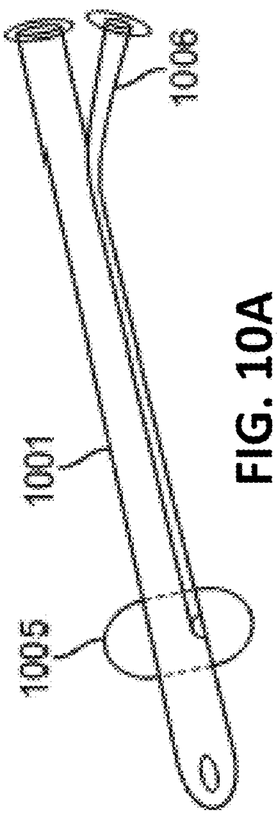
FIGS. 10A-D show various examples of single-use articulating endotracheal tube or Foley catheter with articulation.
Figure 10B:
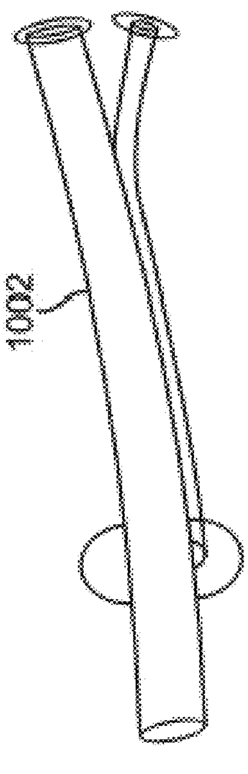
Figure 10C:
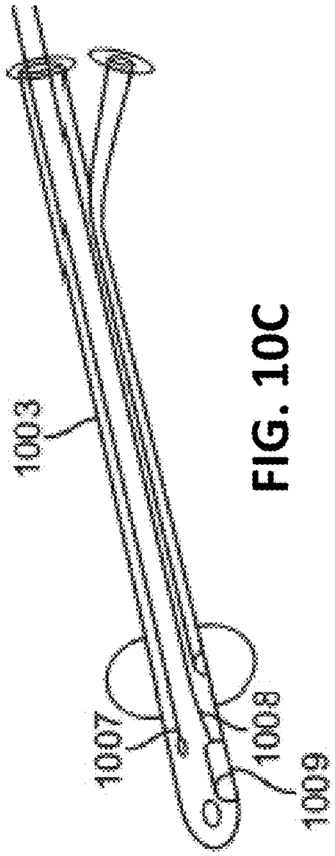
Figure 10D:
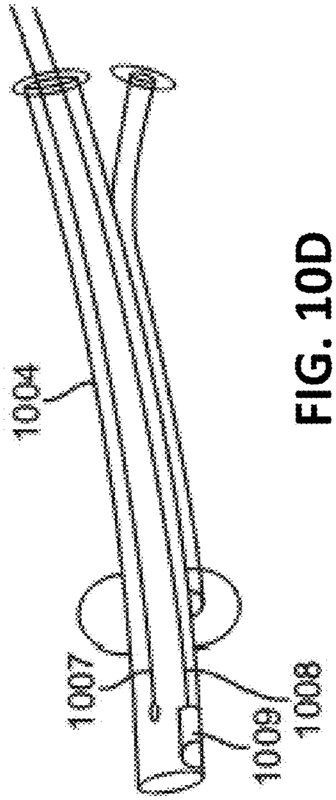

FIGS. 9A-E show various exemplary embodiments of endoscopes with an articulation section. In some cases as shown in FIG. 9A, the distal tip of the catheter or endoscope shaft is articulated/bent in two or more degrees of freedom in order to provide a desired camera view. As illustrated in the example 901, a camera 907 is located at the distal end of the catheter or endoscope shaft 906. The line of sight 908 of the camera may be controlled by controlling the articulation of the distal end. In some embodiments, in stead of or in addition to the articulation, the line of sight of the camera may be adjusted with aid of an optical element (e.g., prism) 909 thereby simplifying mechanical structure of the articulation joints. In some embodiments, the angle of the camera 907 may be adjustable such that the line of sight can be adjusted without articulating the distal tip of the catheter or endoscope shaft. For example, the camera may be oriented at an angle (e.g., tilt) with respect to the axial direction of the tip of the endoscope.

In some cases as shown in FIG. 9B, the distal tip of the catheter or endoscope shaft can be driven by a plurality of pull cables 910. The distal end of the pull cables may be anchored to the tip of the endoscope such that when force is applied, the articulation section/neck portion 911 may be bent into one or more directions. The pull cables as shown in the example 902 can be used in combination with the individually adjustable camera as described in the example 901.

In another example 914 as shown in FIG. 9D, the articulation section of the catheter or endoscope shaft 914 may comprise an articulation structure such as cuts/slot 915. The articulation structure may comprise one or more cuts/slots structure formed at the neck portion/distal portion such that the neck portion can be articulated. By introducing the cuts or slots structure in the shaft or the neck portion of the endoscope directly, articulation can be achieved without extra components (e.g., articulation joints, hinges, pivots, etc.) which advantageously simplifies the geometric design of the articulation section resulting in reduced cost of the disposable endoscope.

Articulation of the flexible catheter or shaft can be affected by the design of the articulation section or stiffness of the catheter. In conventional design, the stiffness or the articulation section is fixed that cannot be adjusted during use. In some embodiments, the elongate member of the present disclosure may have an adjustable stiffness or adjustable articulation section to affect the articulation of the distal portion. In some cases as shown in FIG. 9C, the camera may be located at the distal tip of an inner shaft 912 that can be flexible/compliant and easy to be bent as illustrated in the example 903. The catheter or endoscope shaft as shown 903 may also comprise an outer sheath 913 to provide sufficient support and rigidity to the inner shaft 912. The outer sheath may be more rigid or stiffer than the inner shaft. To achieve articulation, a distal portion of the inner shaft 912 may be extended over the distal end of the outer sheath such that the extended portion may bend into a desired direction at a desired degree. In some cases, the bending degree may be controlled by at least controlling the length of the portion of the inner shaft extended over the outer sheath.

In some cases as shown in FIG. 9E, the adjustable articulation or adjustable stiffness may be achieved with aid of a slidable stiffener 918 as shown in the example 905. For instance, the shaft may comprise a stiffening element and the stiffness of the shaft is adjusted by adjusting a length of the stiffening element inserted into the shaft. The shaft 916 may be, for example, a plastic tube including a channel 917. A stiffener 918 may be inserted inside of the channel 917 and slidable with respect to the shaft 916 to achieve articulation. The assembly 919 may have variable stiffness along the length. The stiffness may be adjusted by adjusting the length of the stiffener 918 inserted into the shaft. For example, greater stiffness may be achieved by inserting greater length of the stiffener into the shaft.

Endotracheal tube and Foley catheters have been widely used in airway management and emptying the bladder. An endotracheal tube is a flexible plastic tube that is placed through the mouth into the trachea (windpipe) to help a patient breathe. The endotracheal tube is then connected to a ventilator, which delivers oxygen to the lungs. In urology, a Foley catheter is a flexible tube that a clinician passes through the urethra and into the bladder to drain urine. Such devices have been difficult to insert into the patient body due to the lack of stiffness and articulation capability of the tip, particularly when they are inserted through natural curvature of the patient anatomy, e.g., from nose/mouse to larynx, from urethra to prostate. It is desirable to provide an articulating intubation or Foley catheter with direct visualization for maneuverability and confirmation of the anatomy.

In an aspect of the present disclosure, a low-cost, single-use, articulating endotracheal tube and articulating Foley catheter is provided. The articulating endotracheal tube and articulating Foley catheter may also have visualization capability.

FIGS. 10A-D show various examples of single-use articulating endotracheal tube or Foley catheter with articulation 1003, 1004. The articulating endotracheal tube or Foley catheter with visualization may be designed to achieve improved performance at reduced cost. As described above, the conventional endotracheal tube 1001 in FIG. 10A or the Foley catheter 1002 in FIG. 10B may comprise a balloon 1005 and a suction line 1006. The provided single-use articulating endotracheal tube 1003 in FIG. 10C and single-use articulating Foley catheter 1004 in FIG. 10D may include a camera 1009 located at the distal portion of the tube. The camera 1009 may be connected to a proximal end via a cable 1008 for transmitting image signals. The articulation of the tube may be controlled by one or more pull wires 1007. Similar to the single-use endoscope design, a distal end of the pull wires may be anchored to the distal portion of the tube to apply force.

Figure 11A:
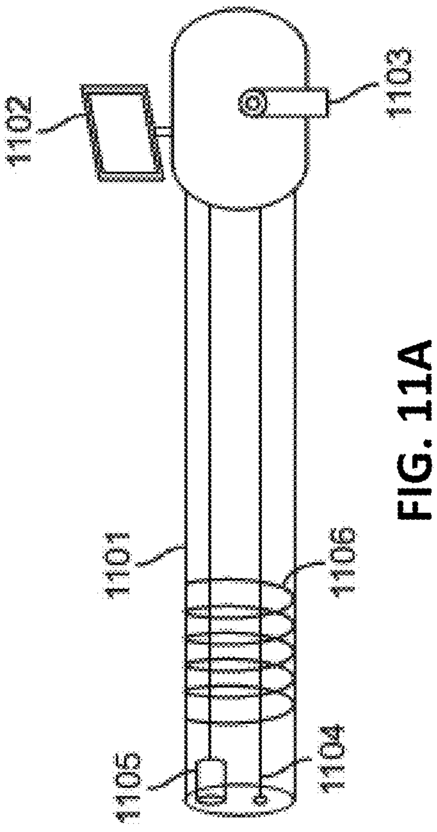
FIGS. 11A-C show an example of an articulating inner guide that can be assembled with existing endotracheal tube or Foley catheter.
Figure 11B:
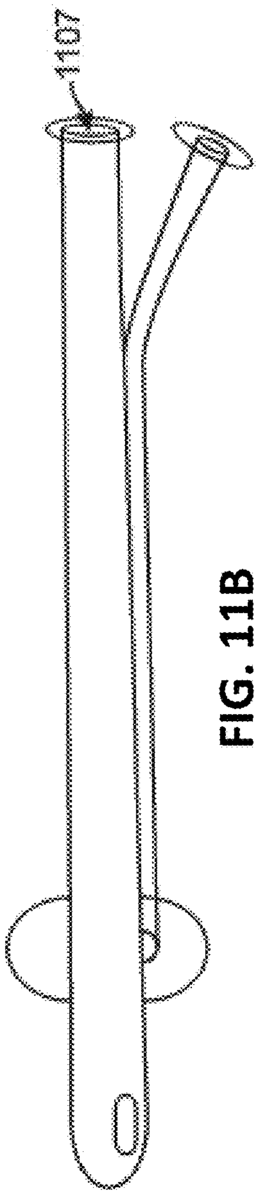
Figure 11C:
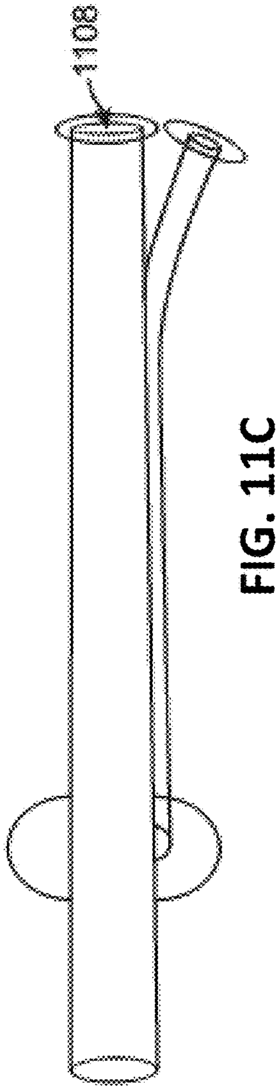

In some embodiments, the articulation and vision capability to an endotracheal tube or Foley catheter may be provided by a separate articulating device. FIGS. 11A-C show an example of an articulating inner guide 1101 that can be assembled to existing endotracheal tube 1107 in FIG. 11B or Foley catheter 1108 in FIG. 11C to provide articulation and vision capabilities.

In some cases, the articulation and vision capability may be provided by a separate articulating inner guide 1101. The articulating inner guide 1101 may be inserted through a channel of the existing endotracheal tube 1107 or Foley catheter 1108. The articulating inner guide 1101 may have a tubular body comprising a cylinder with an outer wall and a central lumen. The outer wall may be adapted to the channel of the existing endotracheal tube 1107 or Foley catheter 1108. The articulating inner guide 1101 may comprise a camera 1105 located at the distal portion and image signals may be transmitted to a display 1102 located at the proximal end via a cable. The articulation may be achieved with aid of one or more pull wires 1104 such that when force is applied to the distal portion of the inner guide through the pull wires, an articulation section 1106 of the inner guide may be bent. The articulation section and the articulation control mechanism of the inner guide can be the same as those as described elsewhere herein. In some cases, the proximal end of the inner guide may also include a user interface 1103 (e.g., lever, knob) for the articulation control. In some cases, both the instrument (e.g., endotracheal tube or Foley catheter) and the endoscope are disposable.

In some embodiments, the present disclosure provides endoscopes with integrated instruments. Traditionally, instruments such as graspers, scissors, baskets, snares, curette, laser fibers, stitching tools, balloons, morcellators, various implant or stent delivery devices, and the like are provided as separate pieces from the endoscope. The above-mentioned instruments can be used in varieties of endoscopies with different kind of endoscopes such as: NeuroendoScope, EncephaloScope, OphthalmoScope, OtoScope, RhinoScope, LaryngoScope, GastroScope, EsophagoScope, BronchoScope, ThoracoScope, PleuroScope, AngioScope, MediastinoScope, NephroScope, GastroScope, DuodenoScope, CholeodoScope, CholangioScope, LaparoScope, AmioScope, UreteroScope, HysteroScope, CystoScope, ProctoScope, ColonoScope, ArthroScope, SialendoScope, and Orthopedic Endoscopes. For example, morcellators can be used in gynecology and rhinology to treat polyps. Balloons can be used to do sinuplasty in rhinology. Certain implants or stents can be used to treat fluid behind the ear drums (tympanostomy), open the sinus ostium, or treat benign prostatic hyperplasia (BPH) by opening the cannel at the prostate. A stitching mechanism can be used to do suture inside the stomach. Laser fibers can be used to do ablation or coagulation in urology, gynecology, and various others.

Traditional endoscopes can be large in size (e.g., a few millimeters to a few centimeters in outside diameter). In order to accommodate any of the above-mentioned instrument, a working channel in the endoscope is usually required so the instrument can pass through. In some cases, more than one working channel is required in order to allow multiple instruments to pass through at the same time. Such design may result in an increased overall size of the endoscopes. It is desirable to provide single-use endoscopes with integrated instruments. The present disclosure provides an integrated endoscope and instrument with reduced overall size of the device.

In some embodiments, a low-cost, single-use endoscope with integrated instrument for treatments in various applications (e.g., bronchoscopy, urology, gynecology, arthroscopy, ENT, gastro-intestine endoscopy, etc.) is provided.

Figure 12A:
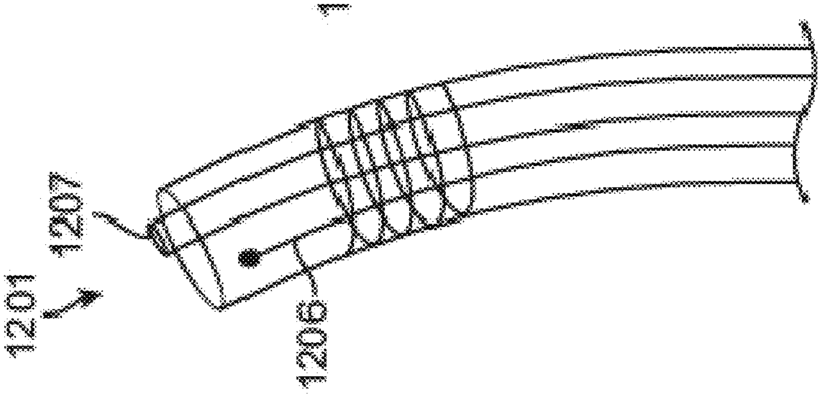
FIGS. 12A-E show examples of integrated devices combining articulating waterjet device and morcellators with single-use endoscopes.
Figure 12B:
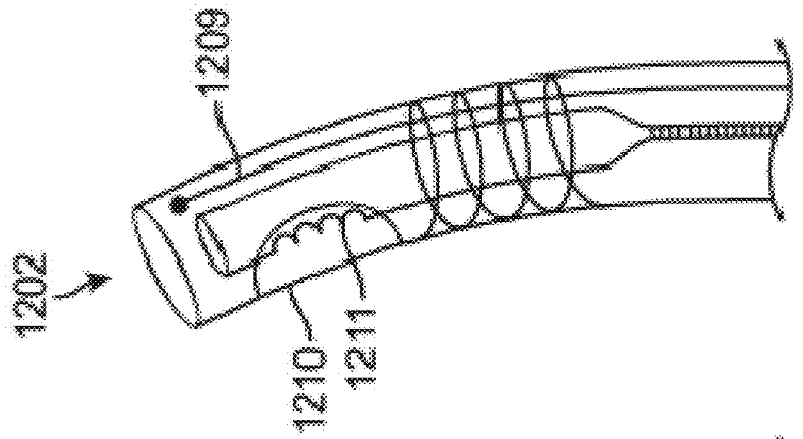
Figure 12C:

FIGS. 12A-E show examples of integrated devices combining instruments and single-use endoscopes. In the illustrated example, the combined device may include an articulating waterjet device or morcellators combined with a single-use endoscope. As illustrated in the example 1201 of FIG. 12A, an articulating waterjet device may comprise a waterjet 1207 and one or more driving mechanism 1206 (e.g., pull cables) for articulation. A morcellator 1202 may comprise an outer tubing 1210 and an inner tubing 1211. In some cases as shown in FIG. 12B, the morcellator 1202 may also comprise one or more driving mechanism 1209 (e.g., pull cables) for articulation.

Figure 12D:
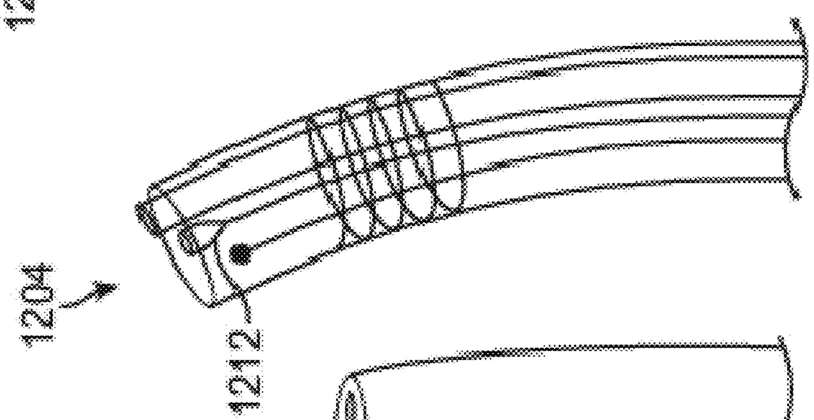
Figure 12E:
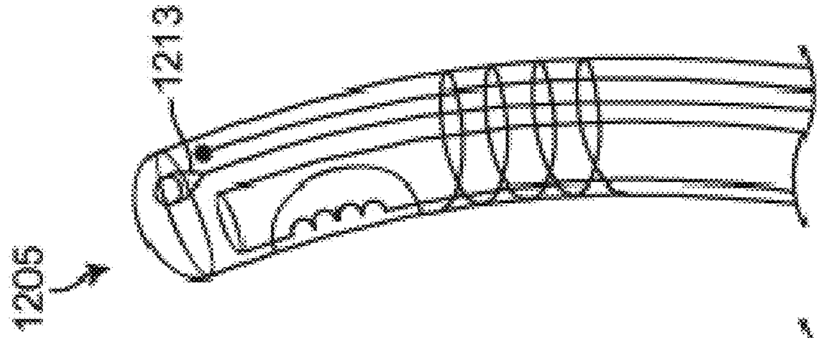

The articulating waterjet 1201 may be integrated with an endoscope 1203 to form an integrated device 1204 as shown in FIG. 12D. The integrated device 1204 may be single-use with a built-in camera 1212 located at the distal end of the device. The camera 1212 may reside next to the distal end of the waterjet device. Similarly, the morcellator 1202 can be integrated with the endoscope 1203 to form an integrated device 1205 as shown in FIG. 12E. The device may comprise a camera 1213 located at the distal end of the integrated device.

Traditional flexible endoscopes may have long and flexible shafts. Because the shafts are flexible, once they are inserted into the patient, it can be difficult to know the accurate location of the flexible endoscope tip inside the patient body. Although the flexible endoscopes provide a first-person/camera view at the clinical site inside the patient, the localization of the flexible endoscope tip relative to the global reference frame or the patient body is not available. Without knowing the accurate location of the flexible endoscope tip with respect to the patient body, surgical operations are difficult to perform and can pose clinical hazards to the patients being treated. It is desirable to provide endoscopes with localization capability.

In some embodiments, a low-cost endoscope with locating features is provided. The endoscope may be single-use can be applied for treatments in various applications (e.g., bronchoscopy, urology, gynecology, arthroscopy, ENT, gastro-intestine endoscopy, etc.). The provided endoscope may integrate one or more location sensors or position sensors to accurately track the position of the distal tip of the endoscope. Various types of positions sensors such as electromagnetic (EM) sensors, FBG—Fiber Bragg Grating, may be integrated to the endoscope. The endoscope with localization capability may be designed with a reduced overall size and may be provided at reduced cost.

Figure 13A:
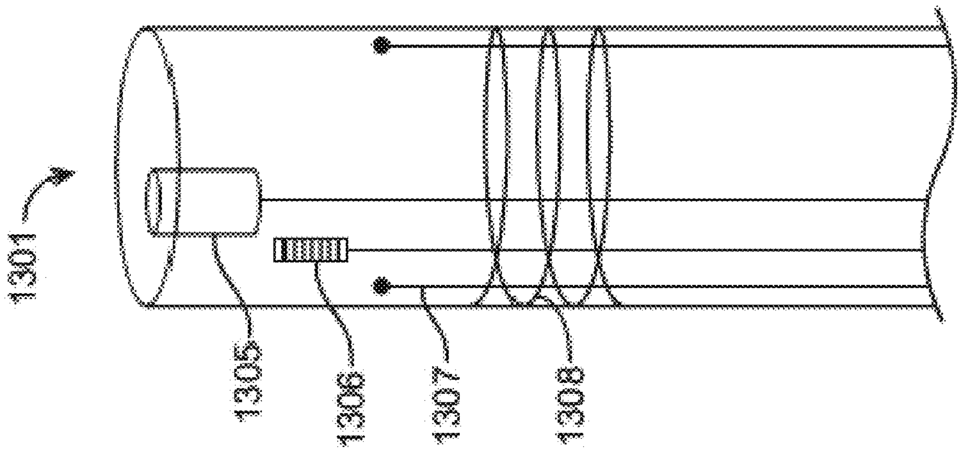
FIGS. 13A-D show examples of endoscopes with integrated localization/position sensors.
Figure 13B:
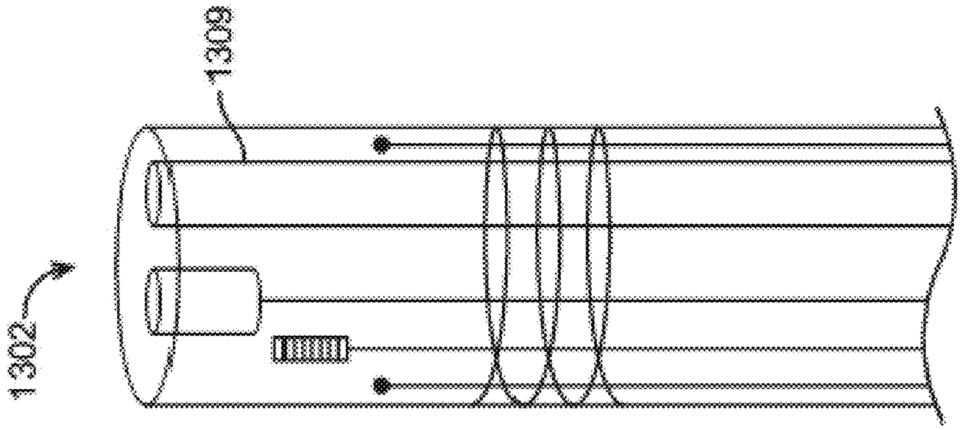
Figure 13C:
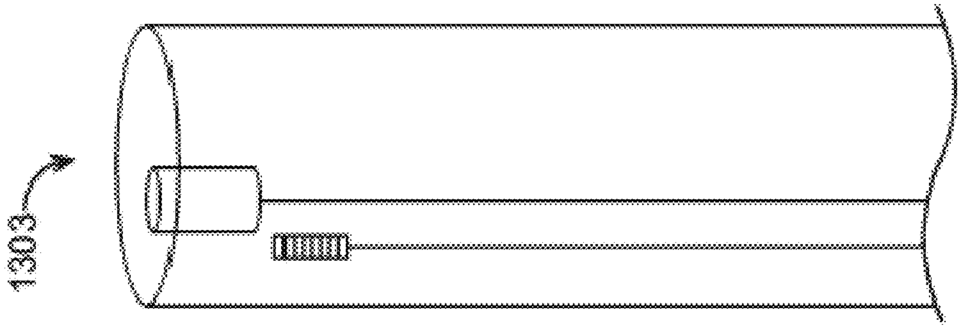
Figure 13D:
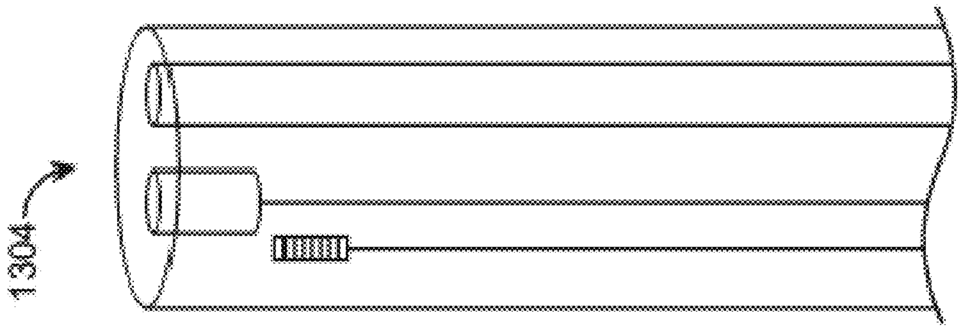

FIGS. 13A-D show examples of endoscopes 1301, 1302, 1303, 1304 with integrated localization/position sensors. In the illustrated examples 1301, 1302 of FIGS. 13A-B, the endoscope may or may not comprise a working channel 1309. The endoscope may include one or more integrated positioning sensors such as electromagnetic (EM) sensors 1306. The one or more sensors may be embedded at the distal tip of the endoscope and an EM field generator may be positioned next to the patient torso during procedure. The EM field generator may locate the EM sensor position in 3D space or may locate the EM sensor position and orientation in 5D or 6D space. This may provide a visual guide to an operator when driving the endoscope towards the target site. The endoscope 1301, 1302 may also comprise a camera 1305 located at the distal end, and one or more articulation driving mechanism 1307 (e.g., pull cables) to control the articulation section 1308 of the endoscope. In some cases, the catheter of the endoscope may be semi-rigid or compliant such that the deformation of the catheter may not be accurately tracked. For example, a semi-rigid endoscope without working channel 1303 as shown in FIG. 13C or with working channel 1304 as shown in FIG. 13D may have an integrated EM sensor such that the location of the distal tip of the catheter can be tracked.

Figures 14A, 14B, 14C, 14D:
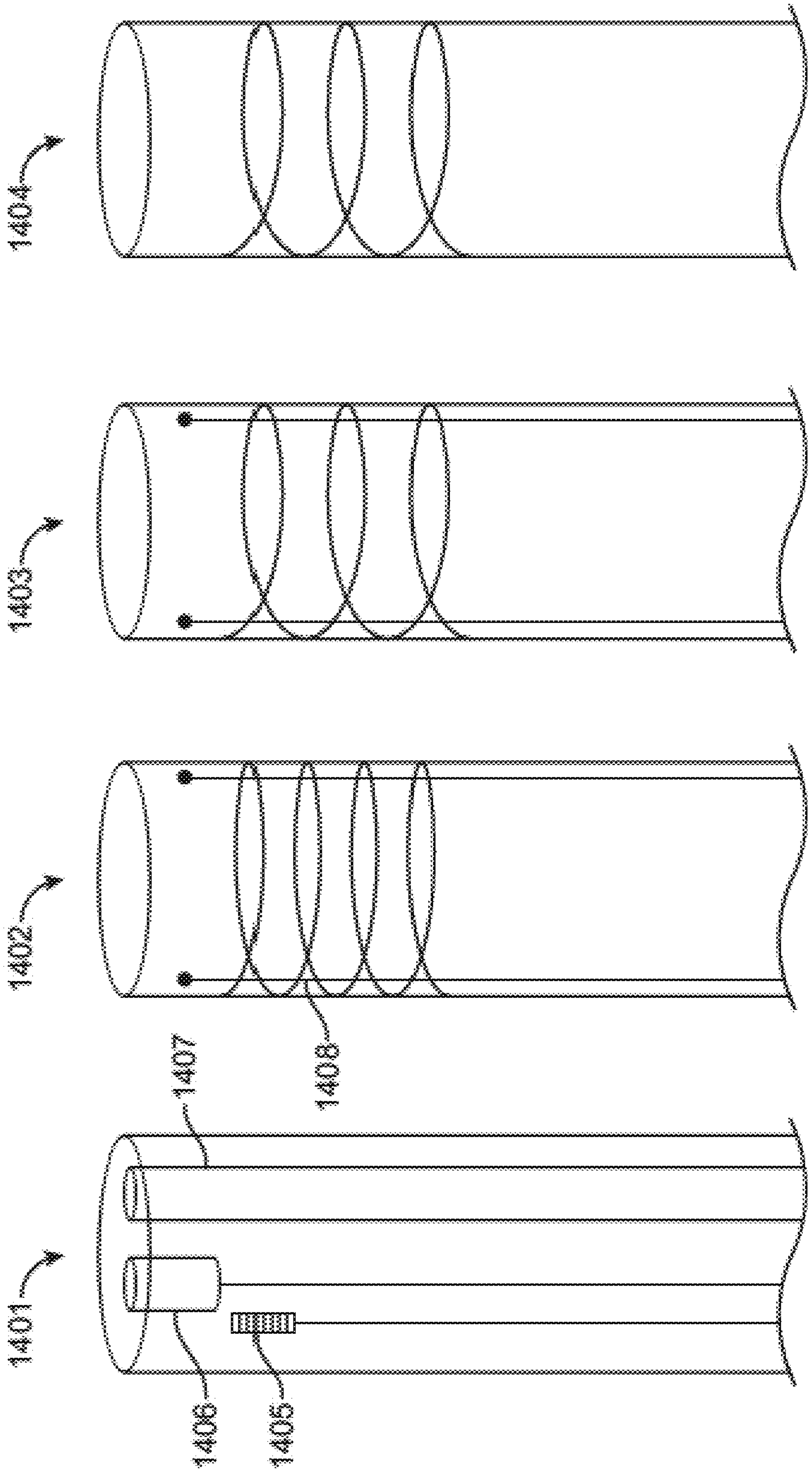
FIGS. 14A-D show an example of an endoscope that is provided with an external guiding element for steerability and control.

In some embodiments, external endoscope guiding elements with articulation capabilities may be provided for navigated procedures. FIGS. 14A-D show an example of an endoscope 1401 that is provided with an external guiding element 1402, 1403, 1404 for steerability and control. In some cases, the catheter or shaft 1401 as shown in FIG. 14A may comprise a camera 1406, a positioning sensor 1405, a working channel 1407 or other structures/components as described elsewhere herein. In some cases, the existing endoscope 1401 may have limited articulating capabilities such as lack of built-in articulating features or insufficient rigidity. The endoscope 1401 can be assembled with one or more modular guiding elements 1402, 1403, 1404 for steerability and control.

In some embodiments, each of the external guiding elements 1402 in FIG. 14B, 1403 in FIG. 14C, 1404 in FIG. 14D may have a tubular body comprising a cylinder with an outer wall and a central lumen. In some cases, each of the external guiding elements 1402, 1403, 1404 may comprise an articulation control mechanism (e.g., pull cables) 1408 and an articulation section. Each of the external guiding elements can be individually controlled for articulation. In some cases, the catheter 1401, the one or more external guiding elements may be removably attached to a handle component. The handle component can be the same as the handle component as described elsewhere herein. For example, a user interface (e.g., lever) for controlling the articulation of the one or more external guiding may be located at the handle component or the disposable elongate member.

The lumen of the external guiding element may be adapted to receive the catheter or an inner guiding element. For instance, the catheter or endoscope shaft 1401 may be inserted through the lumen of the external guiding element 1402 and may be fixed to at least the distal portion of the external guiding element 1402. In some cases, more than one external guide may be assembled with the endoscope concentrically to provide additional degree of articulation. For example, a first external guide 1402 with a first outer diameter (R1) may allow for bending in a first direction, a second external guide 1403 with a second outer diameter (R2, R2>R1) that comes outside of the first external guide may provide bending in a direction different from the first direction, and a third external guide 1404 with a third diameter (R3, R3>R2) that comes from the outside of the second external guide may provide bending in a direction different from the first direction, and the second direction such that the endoscope 1401 can be steerable in at least three directions.

The articulation can be conveniently adjusted by configuring the multiple external guiding elements. The bending direction of the distal end of the shaft may be adjusted by adding or moving the one or more external guiding elements or by configuring a bending direction of the one or more external guiding elements relative to one another. For example, the degree of freedom for bending (e.g., number of bending directions) may be adjusted by adding or removing a number of external guides. In another example, the overall bending directions of the endoscope may be adjusted by configuring the individual bending direction associated with each external guide relative to one another. For instance, each external guiding element may have one degree of freedom for bending, by adjusting the bending axis of an external guiding element relative to the shaft or another bending element, various combinations of the degree of freedom for bending can be achieved. This beneficially provides a modularity design and granular control of the navigation of the endoscope. For instance, when the bending axis/direction of different external guiding elements are aligned with each other, a greater extent of bending in that direction may be achieved, whereas when the bending axis/direction of different external guiding elements are not aligned, additional degree of freedom for bending may be achieved.

Figure 15B:
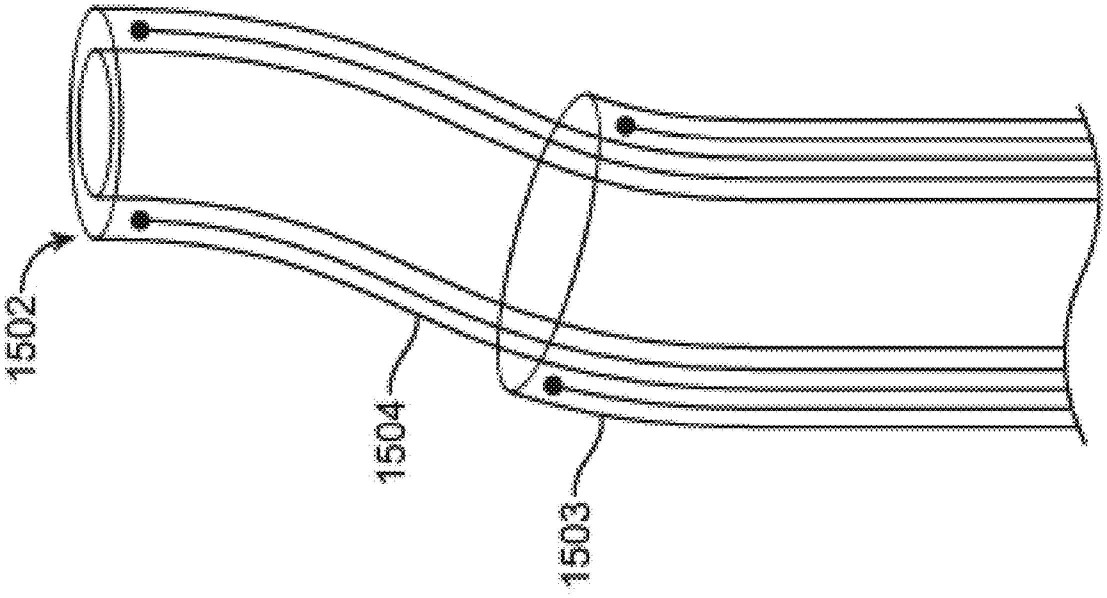
FIGS. 15A-B show an example of endoscope apparatus with external guiding elements, in accordance with some embodiments of the disclosure.
Figure 15A:
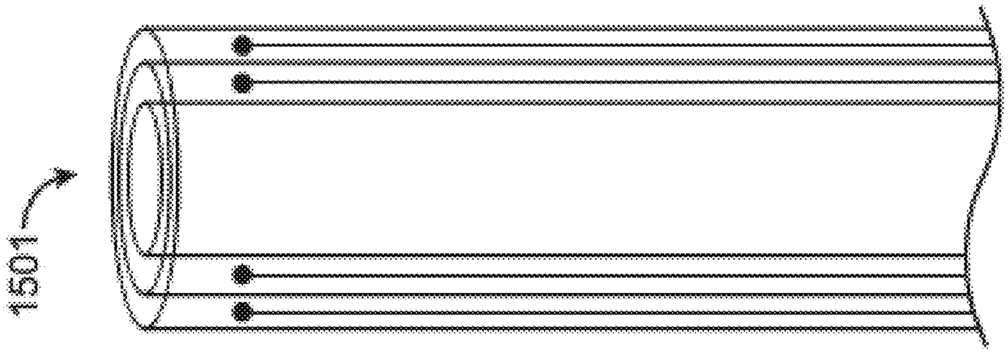

FIGS. 15A-B show an example of assembled endoscope 1501 with one or more external guiding elements. The endoscope external guiding elements 1503 form a pathway for the catheter or endoscope shaft 1502 as shown in FIG. 15B to be inserted through. In some cases, multiple external guiding elements such as the outer guide 1503 and the inner guide 1504 are articulable and can be individually controlled. This may beneficially allow for adjusting the articulation capability of the catheter by adding/removing external guiding elements in an ad-hoc matter.

Figure 16:
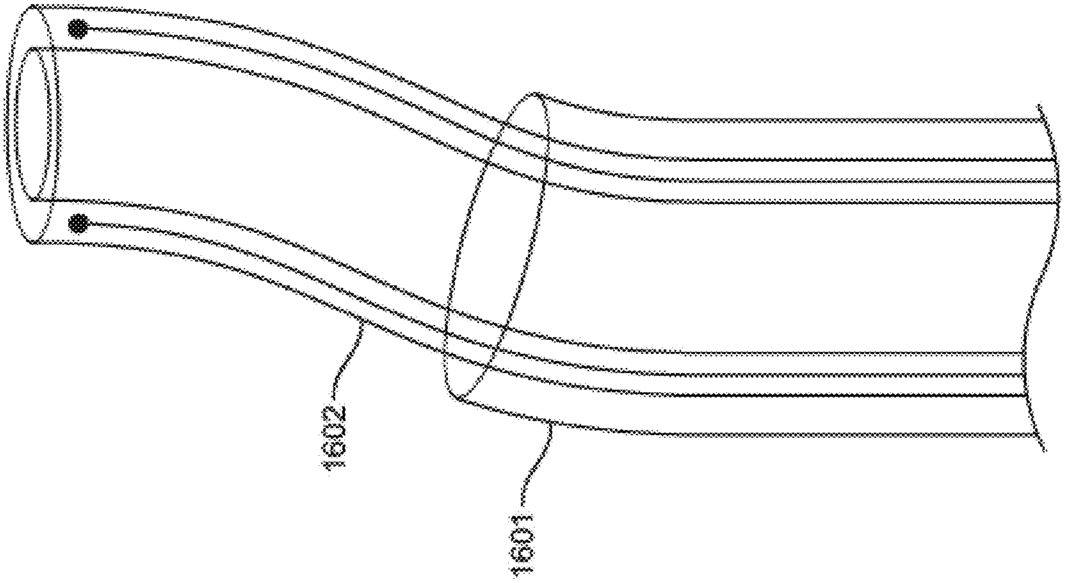
FIG. 16 shows an example of an endoscope with external guiding element.

In some cases, at least one of the external guides is articulable while the other one may be pre-bent with a pre-determined shape. FIG. 16 shows an example of an endoscope assembled with external guiding elements. The outer guide 1601 may be pre-bent at least around the neck section or distal portion and the inner guide 1602 may be articulable.

Figures 17A, 17B, 17C:
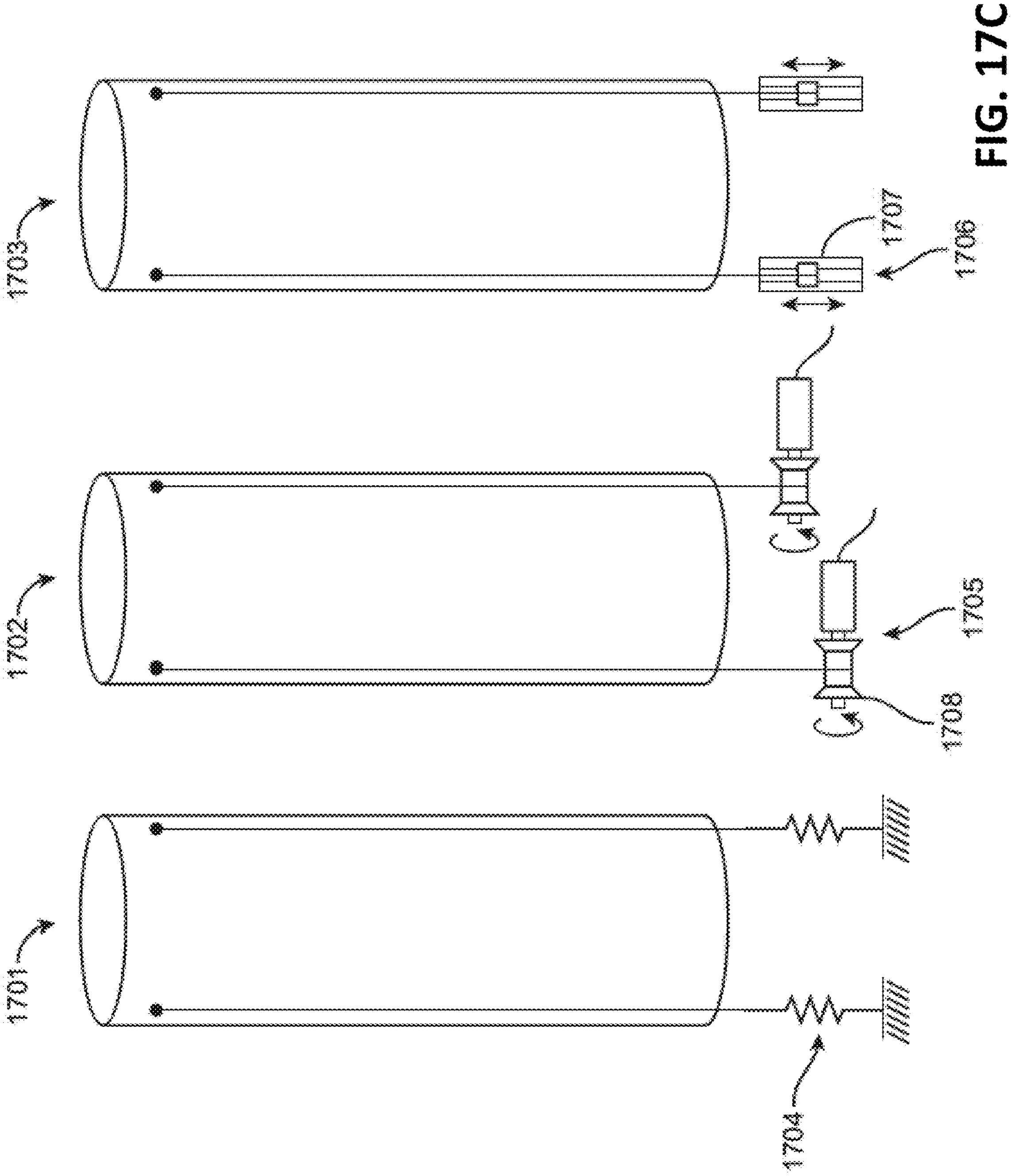
FIGS. 17A-C show various examples of articulation control mechanism for an endoscope and/or the external guiding elements.

FIGS. 17A-C show various examples of the articulation control mechanism 1701, 1702, 1703 for the endoscope and/or the external guides. The articulation control mechanism may be located at the proximal end of the external guides. In some cases, the control mechanism 1704 as shown in FIG. 17A may be passive preload system, such as a spring-based mechanism. The passive preload system maybe attached to a pull cable that is wrapped around a capstan, so that the passive preload system can control the relaxed tension in the pull cable. During operation of the endoscope, friction between the pull cable and the capstan may allow a drive motor to turn the capstan to reel in a length of the pull cable, and capstan friction can apply a maximum tension to the pull cable that depends exponentially on the total angle of wrap the pull cable about the capstan. The force from the passive preload system, e.g., spring force from a spring, and the tension in a relaxed pull cable can therefore be kept relatively low while still being able to produce the high tensions needed for clamping or other movement of the endoscope against resistance. When the motor torque on the capstan is zeroed, the capstan can rotate freely, and the passive preload system can pull in the pull cable and prevent the pull cable from becoming slack. The low relaxed tensions can decrease the forces needed for manipulation of the endoscope, and pull cable friction, which can be particularly problematic in medical instruments with curved or flexible shafts, can be reduced.

In some cases as shown in FIG. 17B, the articulation control mechanism may comprise a set of motors 1705 that are actuated to rotationally drive a set of pull wires of the endoscope. The set of motors may drive the pull wires through pulley assemblies 1708. The number of pulleys may vary based on the pull wire configurations. In some cases, one, two, three, four, or more pull wires may be utilized for articulating the endoscope. Any other suitable mechanical elements in addition to/instead of pulleys such as prismatic linear joint or slide 1707 could be employed as part of the control mechanism 1706 as shown in FIG. 17C.

Endoscopes of the present disclosure can be used to examine the inside of anatomies of subjects, such as animal and human subjects. Subjects may comprise animals such as pig, mouse, dogs, mammals, rodents, monkey, and other animals. Subjects may comprise human subjects, such as patients. The methods and systems provided herein may be used for diagnosing and or treating subjects and/or parts of subjects.

In some embodiments of the present disclosure, a low-cost, single-use, articulating device for diagnosis and treatment is provided. Disposable devices, such as disposable endoscopes may not require post-procedure cleaning, disinfection, and sterilization. Disposable or single-use devices may be disposed after the procedure and save the user valuable time and effort. For example, single-use endoscopes are used only once for each procedure thereby avoiding re-processing after procedure, or risk of causing cross-contamination between patients and reduce infections. In some cases, a single-use endoscope may comprise a disposable catheter removably attached to a re-usable handle component.

In particular, the endoscope of the present disclosure may include an optimal design for the proximal end or handle component at reduced cost. The handle component may be re-usable and provided at reduced cost. The proximal end or handle component may have a unique design such that expensive modules are positioned at the re-usable portion. Additionally, the proximal end may include an improved interface mechanism between the single-use catheter and the handle component thereby providing improved modularity and/or convenient assembly. In some embodiments, the endoscope and the handle component are connected via an interface. For example, the interface may provide electrical connection, mechanical connection and/or illumination alignment.

Figures 18A, 18B:
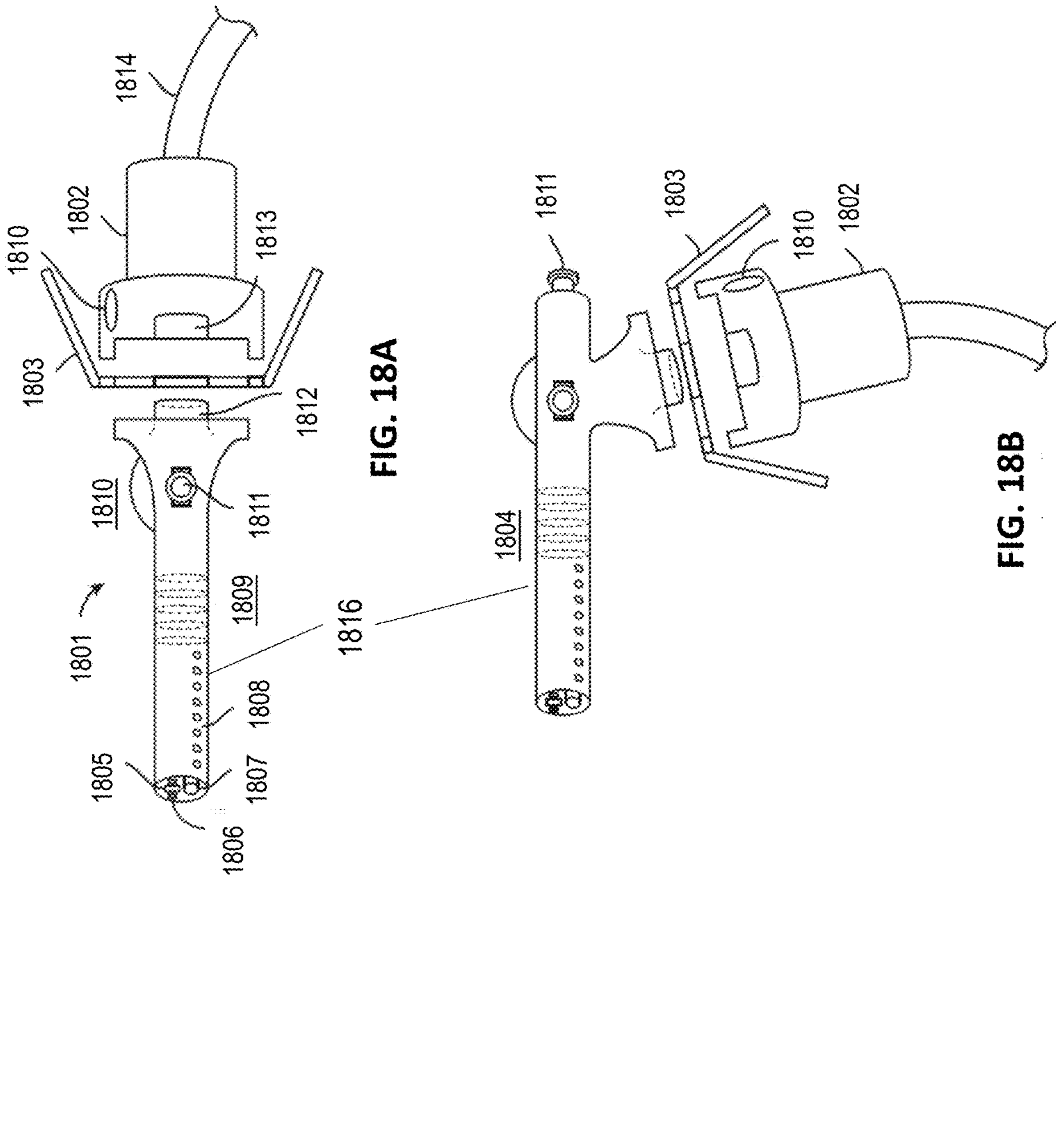
FIGS. 18A-B and FIG. 19 show examples of a single use endoscope (i.e. hysteroscope, cystoscope, resectoscope) with articulatable shaft for diagnosis purpose.

FIGS. 18A-B show examples of a single use endoscope disposable portion 1801, a single use attachable fluid shield 1803, and a reusable hand piece 1802. The endoscope disposable portion may comprise a shaft 1816 and a distal tip where a low-cost camera module 1805 and a illumination module 1806 reside. The camera module can be tilted with a given angle inside the integrated device allowing for a side view of the endoscope. The camera can be tiled at any degree such as at least 0 degree, 12 degree, 18 degree, 30 degree or any number in between.

The shaft 1816 may include a channel 1807 along the length, which may serve as a water channel in diagnosis device or an instrument channel and water channel in a treatment device. One or more fluid access holes 1808 may present along the shaft of the disposable portion. The fluid access holes can be in any shape such as circular, oval, triangular, and the like. Fluid (e.g., water) may return to the proximal end through the one or more access holes.

The shaft may include an articulation portion 1804, 1809 as shown in FIG. 18B and FIG. 18A. In some cases, one or more of the fluid access holes 1808 as described above may also enable the articulation. The one or more fluid access holes may be part of the articulation portion. Details about the articulation portion are described in FIG. 2.

In some cases, the proximal end may include an interface 1812. The interface may comprise mechanical interface, an electrical interface and/or fluid management interface. For example, the interface may comprise an articulation control user interface 1810 such as lever or knob for controlling the distal articulation of the endoscope. In another example, the interface may include a connector such as lures or valves 1811 for air, vacuum, or fluid control and/or flow management. Any suitable irrigation and aspiration system may connect to the endoscope through the connector 1811 (e.g., lures or valves). For example, the irrigation system can inject fluids such as saline and the aspiration system may aspire mucus, saline or other material out of the airways. In a further example, the interface may include electronics for illumination source and imaging control. For instance, an imaging control module may comprise one or more processors and electronics for processing the image signal or performing other operations related to image acquisition.

The interface 1812 may include a mechanical and electrical connection. The interface may include a mechanical interface and an electrical interface. The mechanical interface may allow the endoscope to be releasably coupled to the hand piece, or a control mechanism (e.g., instrument driving mechanism). For instance, the handle piece 1802 can be attached to the endoscope via quick install/release mechanism, such as magnets and spring-loaded levels. In some cases, the endoscope may be coupled to or released from the hand piece manually without using a tool. In some cases, the connection 1813 of the hand piece may provide electrical connection allowing for electric power and data transmission between the electronics located at the hand piece and the endoscope.

Figure 19:
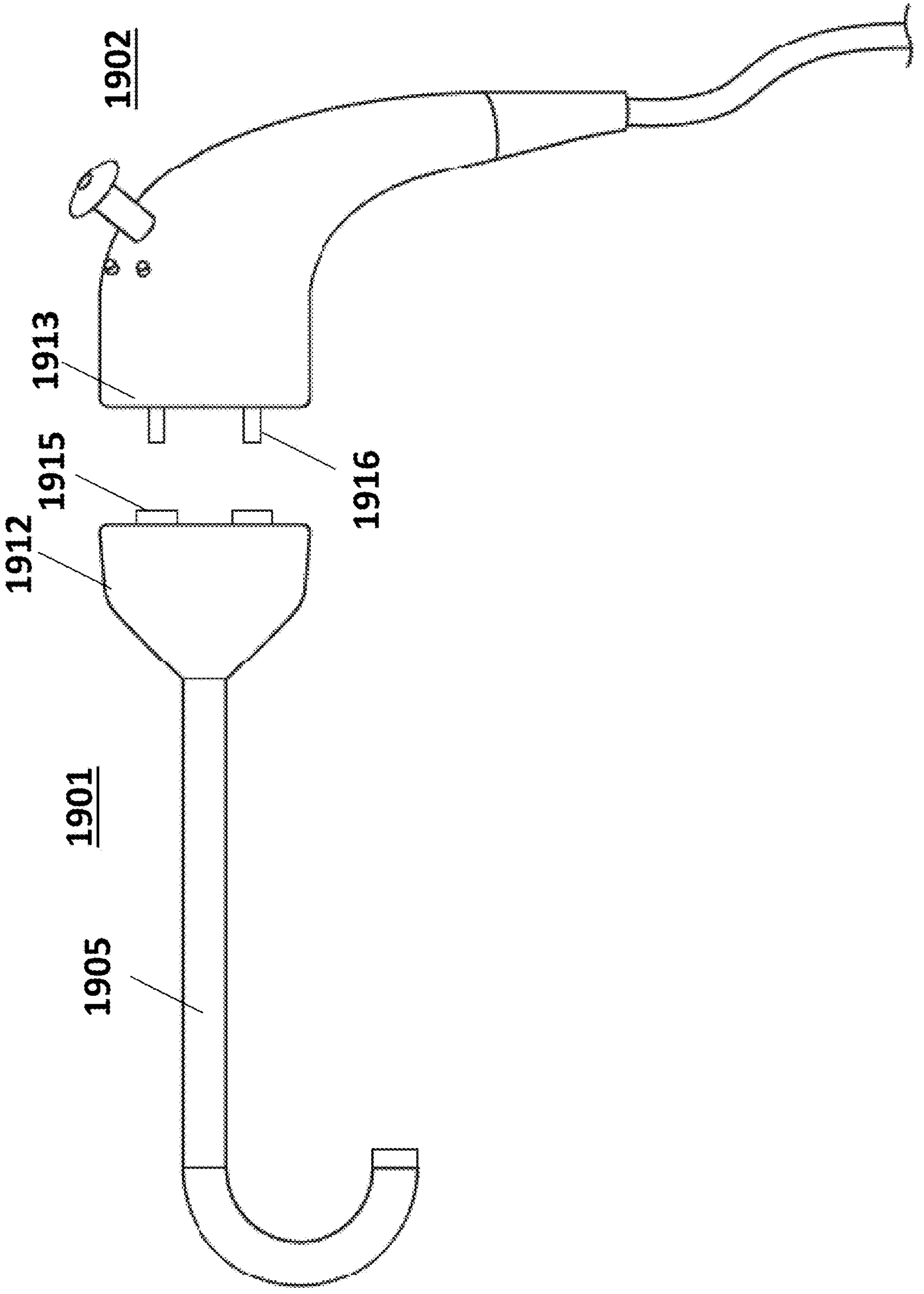

In alternatively embodiments, the hand piece may be reusable with integrated motors that deliver rotary or linear motion to the shaft/flexible instrument. As shown in FIG. 19, the endoscope 1901 may also be releasably coupled to the hand piece 1902 via an instrument driving mechanism of the connection 1913. The instrument driving mechanism may comprise a set of motors that are actuated to rotationally drive a set of pull wires of the catheter/shaft 1905. The interface 1912 of the endoscope may be mounted onto the instrument drive mechanism so that its pulley assemblies 1915 are driven by the set of motors (connecting to the shaft of the motors 1916). The number of pulleys may vary based on the pull wire configurations. In some cases, one, two, three, four, or more pull wires may be utilized for articulating the catheter/shaft 1905.

The reusable handle 1902 may be controlled by a user by interfacing with an electrical joystick and buttons that command the motions of the electrical motors 1916, which then transfer motion to the single use instruments via the interface 1912, which couples to the connection 1913 of the reusable handle.

Referring back to FIG. 18, the device may optionally comprise a single use, attachable fluid shield 1803. The disposable portion 1801 can connect to the hand piece 1802 with or without the fluid shield. The fluid shield can also be utilized in the embodiments described in FIG. 19. Details about the fluid shield are described later herein. In some embodiments, the hand piece may track the gravity direction by including an electromagnetic (EM) tracking device with an embedded EM sensor 1810 inside the disposable portion or the hand piece. Details about gravity direction tracking are described later herein.

The hand piece may be a wireless handle or a wired handle. A wireless handle may comprise, for example, a power source (e.g., battery pack) and a wireless communication module. The battery pack may be rechargeable or disposable. The power source may provide power to the endoscope and/or electronic components of the endoscope (e.g., camera). The wireless communication module may transmit video signals through secured wireless mechanisms such as WiFi, Bluetooth, RF communication or other forms of communication. The wireless signal may be received by a computer and display the live video from the endoscope. For example, images or videos captured by the camera may be broadcasted to a plurality of devices or systems. In some cases, the hand piece may be designed such that no wires are visible or exposed to operators.

In some cases, the hand piece may be connected to external systems (e.g., computer, display, etc.) via wired communication, e.g., cable 1814. In some cases, the wired cable 1814 may provide power to the endoscope device as well as transmitting the video. Any description about the wired/wireless handle and the components (e.g., power source, communication module) thereof can be applied to other embodiments of hand piece as described elsewhere herein.

Low Cost Articulation Design

Conventional endoscopes may have a flexible shaft that can be articulated by control cables or pull wires. For instance, the distal end of one or more pull wires may be anchored or attached to the distal portion of the flexible shaft, such that operation of the pull wires by a control unit may apply force or tension to the distal portion which may steer or articulate (e.g., up, down, pitch, yaw, or any direction in-between) at least the distal portion (e.g., flexible section) of the flexible shaft. Traditional articulating structures often require use of additional elements such as a plurality of interconnected segments, pivots, hinges, and the like to achieve articulation. However, such articulating structures can be difficult to clean and/or sterilize because of the complex geometric structures.

In an aspect of the present disclosure, an improved articulation section design for endoscopes are provided. The articulation section may be comprised of low cost, easily mass produced articulation features that allow the distal end of the endoscope to be bent in a desired direction by one or more control cables.

FIGS. 20A-I show examples of articulation shaft designs. Such articulation shaft designs may beneficially lower the cost so that the disposable portion of the endoscope can be single-use. In some embodiments, one or multiple pull wires 2008 may be attached to the distal portion of the endoscope. In the case of multiple pull wires, pulling one wire at a time can change the orientation of the distal tip to pitch up, down, left, right or any directly needed. In the case of using only one pull wire, the inner channel 1807 may have a higher bending stiffness compared to the outer shaft of the endoscope. The inner channel may serve as a natural spring to anti-react to the motion from the outer shaft of the distal tip. When the single pull wire is released, the endoscope tends to be straightened up due to the existence of the inner channel and its higher bending stiffness.

Figures 20A, 20B, 20C, 20D, 20E, 20F, 20G, 20H, 20I:
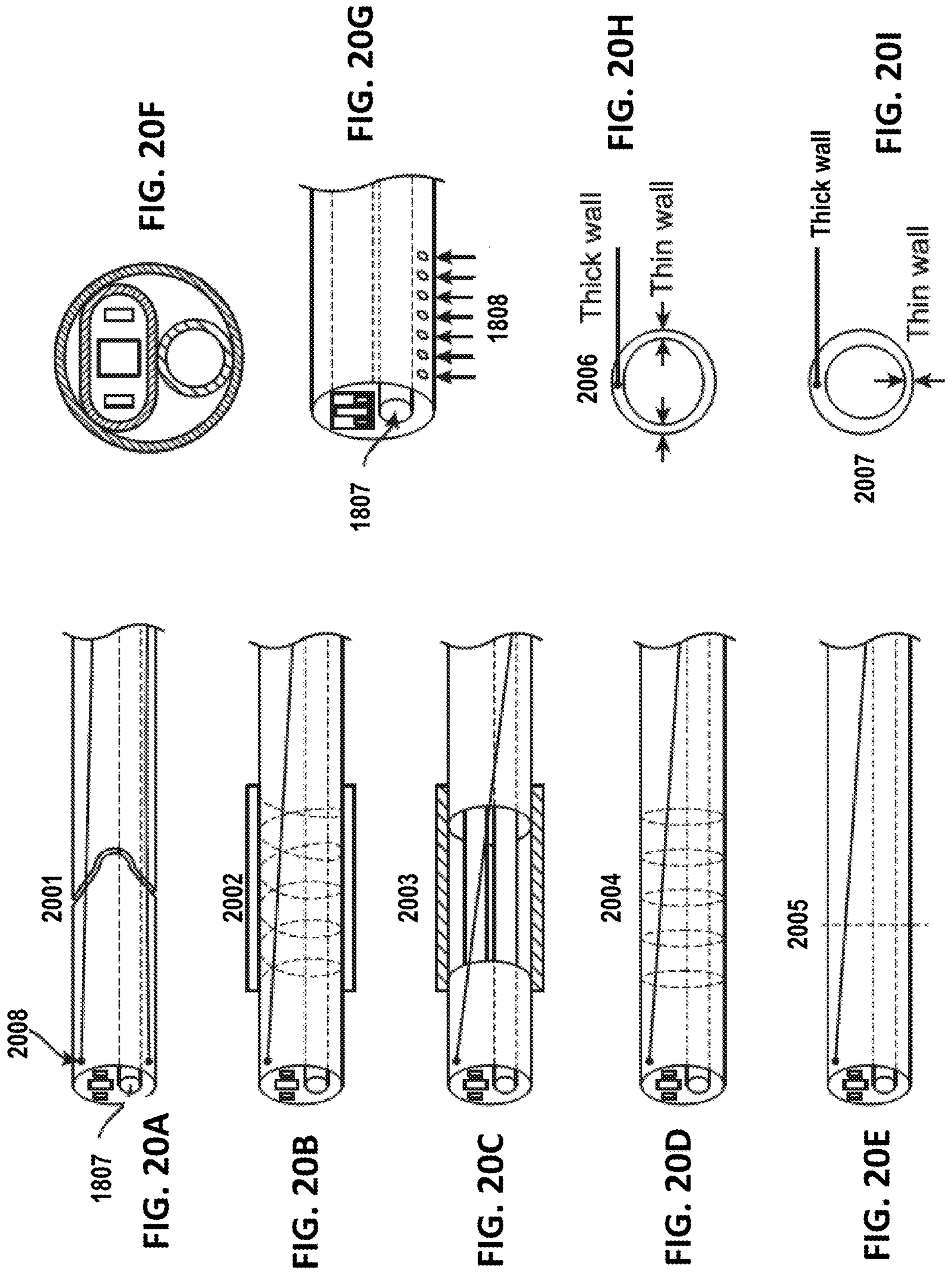
FIGS. 20A-I show examples of various low-cost designs of an articulatable shaft.

In one embodiment as shown in FIG. 20A, the articulation portion of the shaft may include a hinge joint 2001. The distal portion of the shaft may have a cutout of a hinge shape. It matches the proximal side of the shaft with the complementary shape.

In one embodiment as shown in FIG. 20B, the articulation portion 2002 of the shaft may have helical shape. The articulation portion may be cut into a helical shape using laser or other manufacturing methods. On top of the helical portion, an over jacket is added to form a smooth surface of the shaft.

Another embodiment of the articulation section 2003 as shown in FIG. 20C may be formed by joining the distal segment of the shaft (e.g., distal portion) and a proximal segment of the shaft using a short outer tube. The outer tube may connect one end of the distal segment to an end of the proximal segment. The outer tube may have lower stiffness compared to the distal segment and the proximal segment of the shaft. For example, the outer tube may be formed from softer (less stiff) materials. When a pull wire is pulled, the softer outer tube may deform and bend due to less stiffness. Depending on the attachment location of the pull wire anchored to the distal segment, the device can be pulled to a certain predefined direction.

In another embodiment as shown in FIG. 20D, the articulation section 2004 may be achieved by cutting out materials of the shaft. The cutout of the material may be designed such that a shape of shaft may be maintained by the remaining structures. When one or more wires are pulled, the articulation section with less materials/cut-out shape may deflect to a predefined direction due to less of structural strength. In some cases, such cutouts may also serve as the fluid access holes as described above.

In other embodiments as shown in FIG. 20E, the articulation section 2005 may be formed by varying the wall thickness of the shaft 2005. The articulation section of the shaft may have variable wall thickness in the cross-section. As illustrated in the examples of FIGS. 20F-I, the articulation section may have cross-sectional views 2006 and 2007 with the wall having a variable thickness such that at least the thickness along one direction is different from the thickness along another direction within the cross-section. One or more pull wires can be embedded into the wall of the distal tip of shaft. When a pull wire is pulled, the shaft may deflect into a direction substantially aligned to the direction of the thinner walls (e.g., indicated by the arrows). Materials of the shaft may be selected (e.g., silicone, soft nylon, etc) to ensure the shaft does not kink or fracture.

Figure 24:
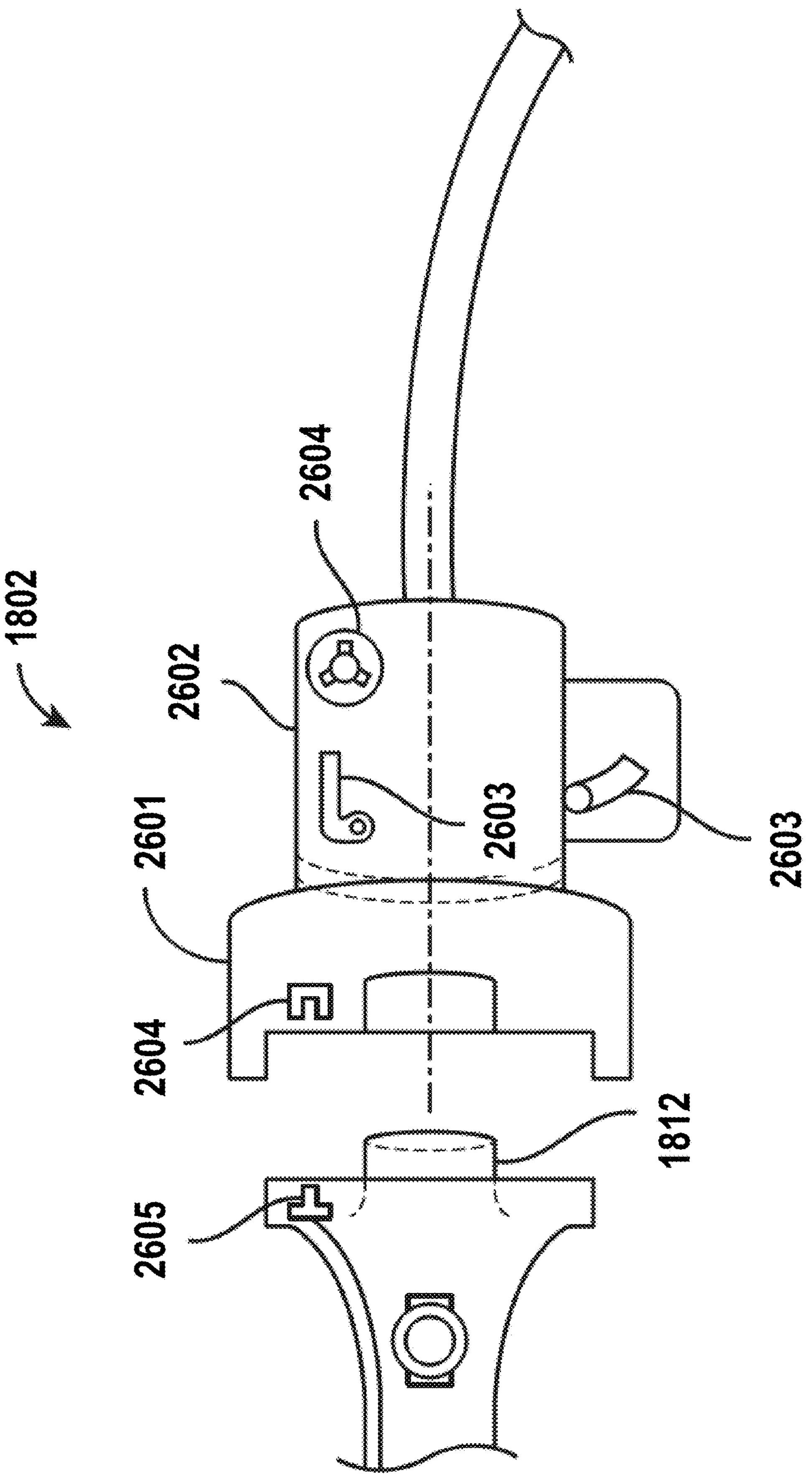
FIG. 24 shows examples of control of the articulation of the shaft on a hand piece.

FIG. 24 illustrates examples of controlling the articulation via a mechanical control mechanism. For example, the mechanical control mechanism may include a pair of latching mechanical structure 2605 and 2604 residing in the disposable portion and the hand piece respectively. In some cases, the latching structures can be a pair of magnets. The latching part located at the disposable portion can be attached to the pull wire with proper tension force. When the disposable portion is connected to the hand piece, the pair of latching parts latches. The latching part located at the hand piece is connected to a user interface such as an actuation knob through internal mechanical structure. The actuation knobs may be, for example, pull trigger 2603, a rotating knob 2604, that can enable relative rotation between the distal portion 2601 of the hand piece 1802 and the proximal portion 2602 of the hand piece. The actuation knobs can be self-lockable to maintain the pull force to articulate the shaft.

The articulation control mechanism may be configured to control the amount of articulation (e.g., deflection degree), and/or the deflection direction. The articulation direction and angle may be controlled by pulling a selected pull wire via the knob rotation. By tracking down the amount of knob rotation using sensor such as digital counter, and the like, the articulation amount/angle can be fed into the computer which keeps tracks of the articulation in real time.

Single Use Water Shield

Figure 22A:
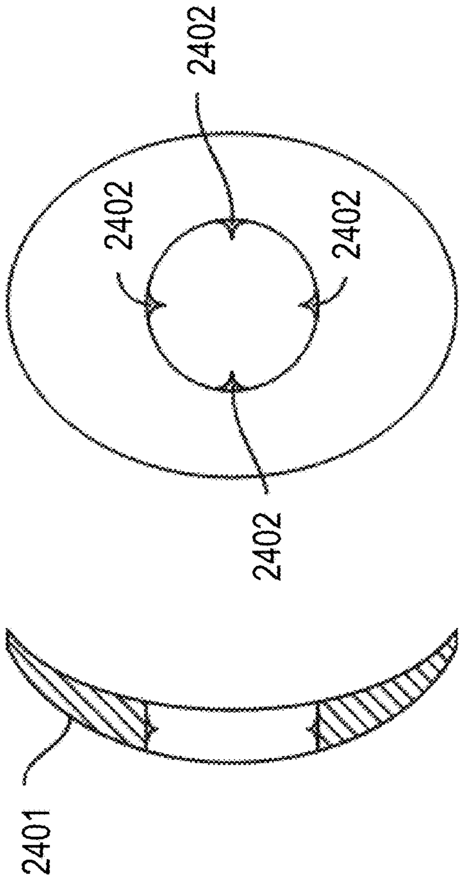
FIGS. 22A-B show examples of a single use fluid shield to avoid splash of patient body liquid to the hand piece or the operator.
Figure 22B:
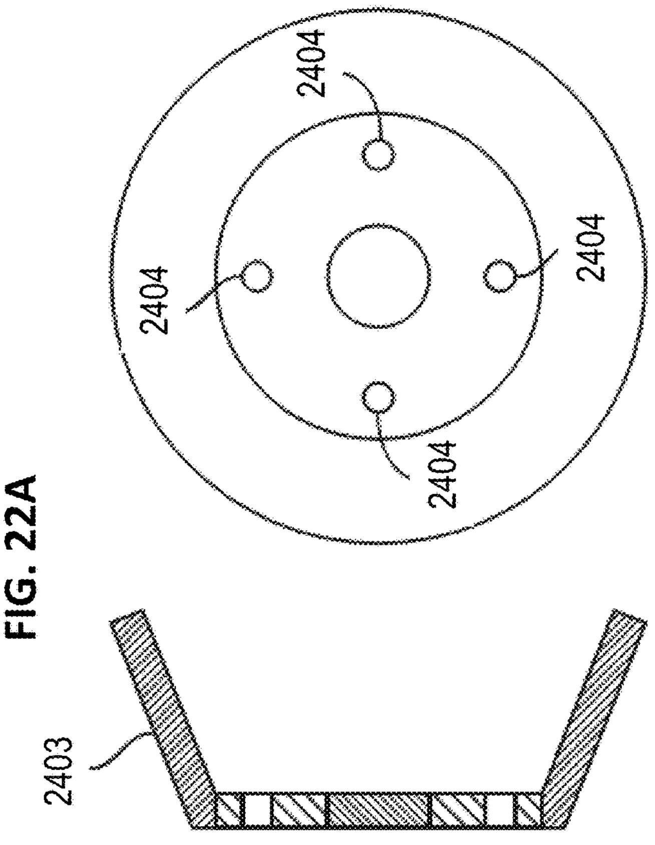

Sterile boundary is critical for surgical procedures. FIGS. 22A-B show examples of sterile single-use water shield designs. A low-cost design is provided to enable the single use of the water shield. Prior to procedure, the water shield 1803 can be assembled to the hand piece 1802 and create a sterile boundary. The distal portion of the water shield is sterile. The disposable portion 1801 of the endoscope is plugged into the handle piece with the water shield.

As illustrated in the example 2401 of FIG. 22A, the water shield may be a medical grade plastic shield molded to a half dome shape. The water shield is the same as the fluid shield as described in FIG. 18. The water shield may have an opening accommodating the disposable portion of the endoscope. The disposable portion of the endoscope may be plugged through the water shied into the hand piece. Along the perimeter of the opening (e.g., center hole), there may be one or multiple protrusions 2402 that may click onto the interface of the disposable portion which further connect to the hand piece.

In another example of FIG. 22B, the water shied 2403 may have substantially a cup shape. The water shield may include a center hole allowing the disposable portion of the endoscope pass through to connect to the hand piece. The water shield may also include one or more engaging holes 2404 around the center hole. These engaging holes may connect to the matching poles on the hand piece thereby prevent a rational movement of the water shield relative to the hand piece. Once the disposable portion is connected to the hand piece, the water shield is further secured without movement at the interface between the handle piece and the proximal end of the shaft.

Gravity Compensation

In endoscopic procedures, the camera view is inside the patient body and all enclosed by anatomic landmarks. Because of no access to the outside view of the patient body, i.e. patient gesture, it is critical to understand which direction gravity is with respect to the camera view. The provided system may be capable of tracking the gravity direction by correlating the device position and orientation to an external device.

FIGS. 21A-E shows one example of a system with gravity direction tracking capability. In some cases, the camera may be located at the distal tip of the shaft. The system may include at least a disposable portion 1801, a hand piece 1802, and a computer with display 2301 in FIG. 21A. In some cases, the gravity direction detected by a gravity sensor is used to correct a view of the image data. One example to track the gravity direction is by including an electromagnetic (EM) tracking device 2302 in FIG. 21B with an embedded EM sensor 1810 inside the disposable portion or the hand piece. The one or more sensors may be embedded at the distal tip of the endoscope and located close to the camera. In some cases, an EM field generator may be positioned next to the patient torso during procedure. The EM field generator may locate the EM sensor position in 3D space or may locate the EM sensor position and orientation in 5D or 6D space. The EM device communicates with the computer through cable or wirelessly. Images on the screen can be corrected based on the gravity information provided by the EM device in a software running on the computer 2301. For example, when the rolling angle of the camera and the respective view of the image may be corrected to align to the gravity direction based on the sensor data. Patient posture relatively to the gravity direction can be input by the computer to allow fine tuning of the gravity compensation precision.

Figure 21A:
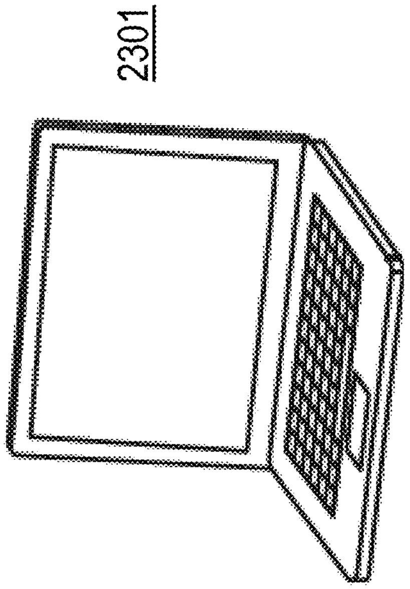
FIGS. 21A-E show exemplary system modules.
Figure 21B:
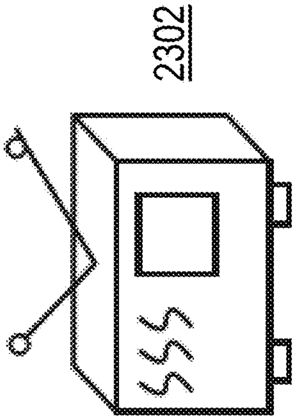
Figure 21C:
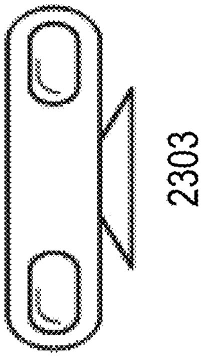
Figure 21D:
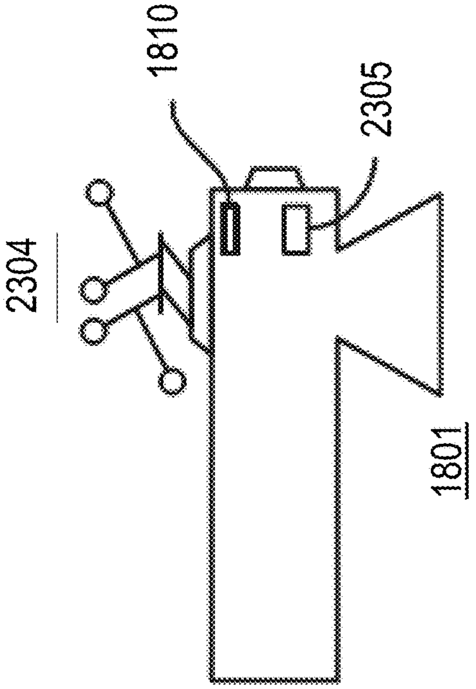
Figure 21E:
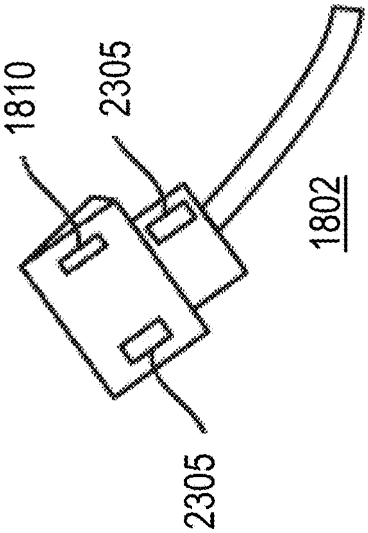

Alternatively, a vision tracking system 2303 in FIGS. 21C-D may allow one or more features 2304 of the disposable portion to be tracked relatively to the gravity direction. These one or more features may include: a customized graphics, structure markers, geometry on the device, or any other visually recognizable features.

In another embodiment, the gravity tracking feature may include use of gravity sensors or other sensors such as IMU, accelerometer, hall sensors, inertia sensors, potentiometers, encoders, and the like. Such sensors may be located at the disposable portion, the hand piece or both. In some cases, the gravity direction is determined based on sensor data collected from the EM sensor located at the handle component and an EM sensor located at the distal end of the elongate member. In some cases, such gravity sensor may reside on the distal and proximal portions of the hand piece respectively if there are relative motions between the distal and proximal portion. These sensors may detect the gravity direction or relative motions between the disposable portion and hand piece or parts within the hand piece and then transmit the information to a processor 2301. There may be a pair of sensors or multiple pairs of sensors. The patient posture can be input by physician to the computer. The provided system may keep track of the gravity direction change by software running on the computer.

In some cases, gravity direction may be tracked by utilizing the anatomical landmarks (e.g., ostium). In some cases, certain clinical landmarks are known to be at specific known location, i.e. two ostiums are on patient left and right, verumontanum is on patient posterior, and the like. Software image capturing and algorithm may correct gravity direction every time the camera view captures such clinical landmarks. Image segmentation algorithm may be used to identify these landmarks and generate a rotating (correction) angle relatively to patient anterior or posterior. Live images or videos may be rotated to be aligned to the gravity direction based on the information. In some cases, at the beginning of the software algorithm, physicians may input the specified gravity direction with respect to the landmark orientation before starting the procedure.

Image Stitching Method

Single-use endoscopes may utilize a low-cost camera module at distal tip. Due to the nature of the low cost, these camera modules may have a limited field of view (FOV), i.e. 90 degrees, 100 degrees, 110 degrees, 120 degrees, etc. Endoscopic surgeries sometimes require physicians to have a good understanding of the whole anatomical structure with an overview of the whole surgical site. One way to implement this feature with low cost and limited FOV camera modules is to use image stitching in software. Stitching images in panorama view may be used to enlarge FOV to provide physician a sense of the global picture.

Figure 23:
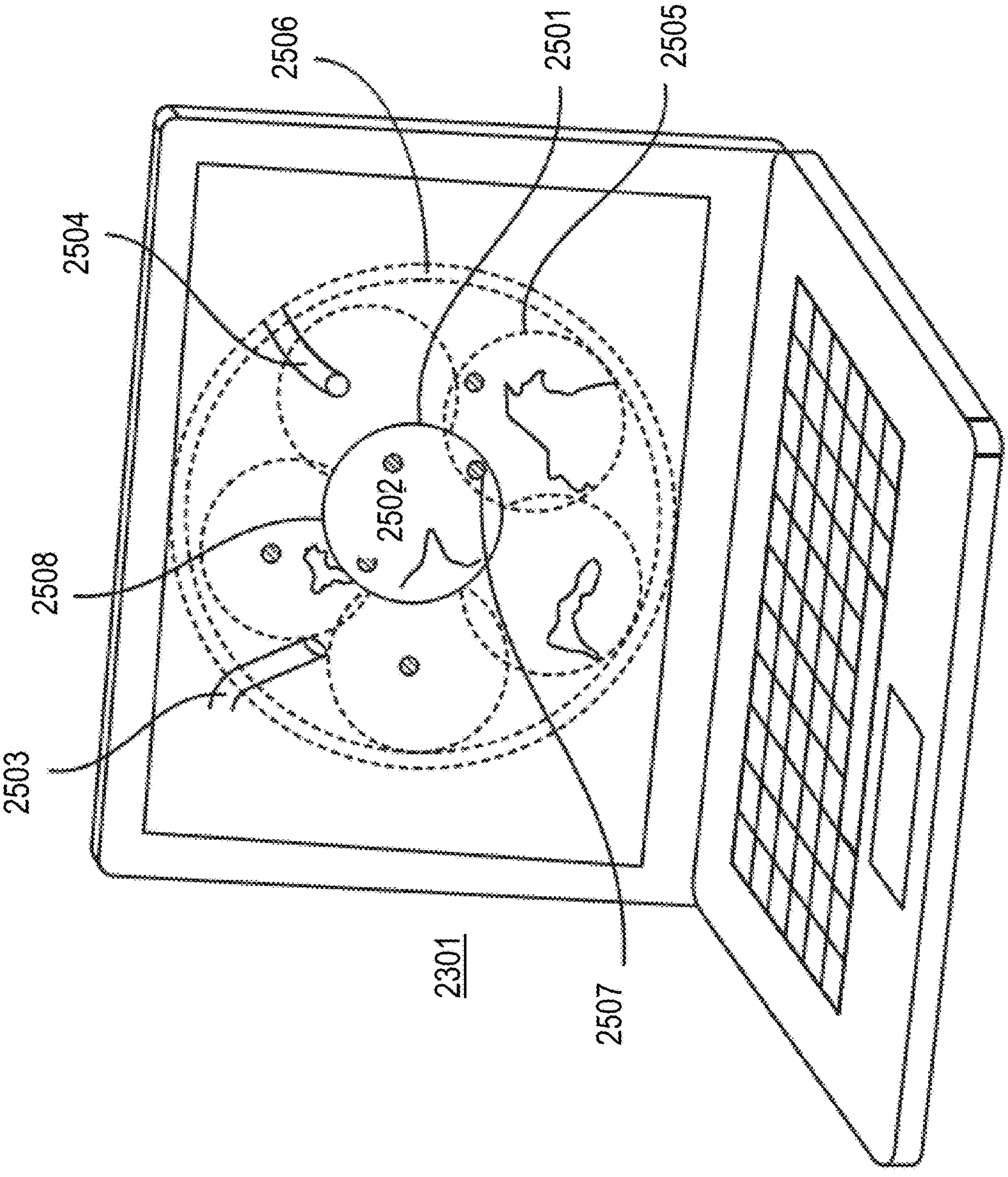
FIG. 23 shows an example of an image stitching capabilities of the system.

FIG. 23 shows an example of a dynamic overview of the whole surgical site on a computer display 2301. The center solid circle 2501 shows a view which is similar to classic endoscopic view in camera. A possible lesion 2502 is identified together with a few solid dark dots. When endoscope is articulated, the view shifts to one of dotted line circles, i.e. 2505. In this view 2505, the same feature 2507 is also identified. By automatically tracking down these features 2507, and by taking into account the amount of articulation from the hand piece, together with the position and orientation of the device through tracking devices like EM tracker 302 or vision tracker 303, the relative locations of the circle 2501 and 2505 is calculated and then these two images can be stitched together. The correction stitching method may require knowledge about the device position and orientation, the articulation amount and the same feature showing up in different views.

Similarly, by scanning through the whole anatomy, one or more dotted circles like 2505 are stitched together using features in different view. The outer double dotted circle 2506 shows a full view of the anatomy. As the distal camera is moving within the anatomy, images or video are acquired at a high frequency e.g., at least 22 fps, 30 fps, 60 fps or higher frequency. Any changes in anatomy or features may be displayed in real-time on the display screen to keep the stitching precise and accurate. As illustrated in the examples, ostium 2503 and 2504 may not be present in the classic view of the endoscope 2501 but can be seen with the stitch image 2506, which advantageously give physicians a good understanding of the landmarks.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. An endoscopic device comprising:

an elongate member comprising a proximal end and a distal end, wherein a camera is located at the distal end of the elongate member, and wherein the elongate member is single-use and comprises a user interface located at the proximal end of the elongate member for controlling an articulation movement of a distal portion of the elongate member, wherein the articulation movement of the distal portion of the elongate member is about a first bending axis;

a handle component removably attached to the proximal end of the elongate member via an interface and wherein the interface provides an electric connection, wherein the handle component is re-usable and comprises electronics for processing data transmitted from the camera; and a first external guiding element removably assembled with the elongate member coupled to the elongate member concentrically such that the elongate member is placed inside the first external guiding element and is movable relative to the first external guiding element, wherein the first external guiding element comprises an articulation control mechanism and is individually controlled to bend the elongate member about a second bending axis, and wherein the second bending axis relative to the first bending axis is configurable such that when the second bending axis is aligned with the first bending axis, an extent of movement about the first bending axis is increased, and when the second bending axis is not aligned with the first bending axis, the first external guiding element is configured to bend the elongate member about the second bending axis, the second bending axis being oriented in a different spatial direction from the first bending axis such that the first external guiding element provides an additional degree of the articulation movement in a bending direction not accessible by movement about the first bending axis alone.

2. The endoscopic device of claim 1, wherein the elongate member comprises a stiffening element that is a slidable stiffener inserted into a channel of the elongate member and is slidable with respect to the elongate member, and wherein a stiffness of the elongate member is adjusted by adjusting a length of the stiffening element inserted into the elongate member.

3. The endoscopic device of claim 1, wherein the interface between the handle component and the proximal end of the elongate member comprises a locking mechanism to secure a mechanical connection between the handle component and the proximal end of the elongate member.

4. The endoscopic device of claim 1, wherein the user interface for controlling the articulation of the distal portion of the elongate member is located at the proximal end of the elongate member.

5. The endoscopic device of claim 4, wherein the user interface comprises a knob, a lever or a button for controlling the articulation of the distal portion of the elongate member.

6. The endoscopic device of claim 4, wherein the user interface further comprises a mechanical structure for flow management of the endoscopic device.

7. The endoscopic device of claim 1, wherein the first external guiding element is removably assembled with the elongate member by removably attaching to the handle component.

8. The endoscopic device of claim 1, further comprising a second external guiding element having a third bending axis.

9. The endoscopic device of claim 8, wherein each of the first and second external guiding elements comprises an articulation control mechanism for controlling an articulation of the corresponding external guiding element about the first bending axis or the second bending axis.

10. The endoscopic device of claim 8, wherein the first, second and third bending axes are different.

11. The endoscopic device of claim 1, wherein a degree of freedom for bending of the distal end of the elongate member is increased by adding an external guiding element or decreased by removing an external guiding element.

12. The endoscopic device of claim 1, wherein the first external guiding element is pre-bent.

13. The endoscopic device of claim 1, wherein the elongate member comprises an articulation section formed at least by one or more fluid access holes.

14. The endoscopic device of claim 1, wherein the handle component comprises an electromagnetic (EM) sensor to detect a gravity direction.

15. The endoscopic device of claim 1, wherein the gravity direction is determined based on sensor data collected from the EM sensor located at the handle component and an EM sensor located at the distal end of the elongate member.

16. The endoscopic device of claim 15, wherein the gravity direction is used to correct a view of the image data.

17. The endoscopic device of claim 15, further comprising a fluid shield connected to the proximal end of the elongate member.

18. The endoscopic device of claim 1, wherein the elongate member comprises an articulation section having a variable wall thickness that affects a direction of the articulation movement of the distal portion of the elongate member.

19. The endoscopic device of claim 1, wherein the elongate member further comprises a working channel for receiving one or more instruments.

* * * * *